United States Patent
Rosi et al.

(10) Patent No.: US 11,389,866 B2
(45) Date of Patent: Jul. 19, 2022

(54) SINGLE-HELICAL GOLD NANOPARTICLE SUPERSTRUCTURES AND METHODS OF MAKING

(71) Applicant: University of Pittsburgh—Of the Commonwealth System of Higher Education, Pittsburgh, PA (US)

(72) Inventors: Nathaniel L. Rosi, Pittsburgh, PA (US); Andrea David Merg, Pittsburgh, PA (US); Soumitra Punekar, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 1252 days.

(21) Appl. No.: 15/842,625

(22) Filed: Dec. 14, 2017

(65) Prior Publication Data
US 2018/0169754 A1    Jun. 21, 2018

Related U.S. Application Data

(60) Provisional application No. 62/435,487, filed on Dec. 16, 2016.

(51) Int. Cl.
| | | |
|---|---|---|
| B22F 1/07 | (2022.01) | |
| C07K 7/08 | (2006.01) | |
| C07D 249/04 | (2006.01) | |
| C07K 17/14 | (2006.01) | |
| B22F 9/24 | (2006.01) | |
| B82B 3/00 | (2006.01) | |
| B22F 1/054 | (2022.01) | |
| B82Y 40/00 | (2011.01) | |
| B82Y 5/00 | (2011.01) | |

(52) U.S. Cl.
CPC .............. *B22F 1/07* (2022.01); *B22F 1/054* (2022.01); *B22F 9/24* (2013.01); *B82B 3/0009* (2013.01); *C07D 249/04* (2013.01); *C07K 7/08* (2013.01); *C07K 17/14* (2013.01); *B22F 1/0553* (2022.01); *B22F 2301/255* (2013.01); *B82B 3/0066* (2013.01); *B82Y 5/00* (2013.01); *B82Y 40/00* (2013.01)

(58) Field of Classification Search
None
See application file for complete search history.

(56) References Cited

PUBLICATIONS

Chen et al. (J. Am. Chem. Soc. 2008, 130, 13555-13557) (Year: 2008).*
Merg et al. (J. Am. Chem. Soc. 2016, 138, 13655-3663) (Year: 2016).*
Zhao et al., "Twisted optical metamaterials for planarized ultrathin broadband circular polarizers," *Nature Communications*, 3:870, 7 pages (May 2012).
Gansel et al., "Gold Helix Photonoc Metamaterial as Broadband Circular Polarizer," *Science*, vol. 325, pp. 1513-1515 (Sep. 2009).
Merg, et al., "Adjusting the Metrics of 1-D Helical Gold Nanoparticle Superstructures Using Multivalent Peptide Conjugates," *Langmuir*, 31 (34), pp. 9492-9501 (2015).
Merg, et al., "Peptide-Directed Assembly of Single-Helical Gold Nanoparticle Superstructures Exhibiting Intense Chiroptical Activity," *J. Am. Chem. Soc.*, 138 (41), pp. 13655-13663 (2016).
Wu, et al., "Unexpected Chirality of Nanoparticle Dimers and Ultrasensitive Chiroplasmonic Bioanalysis," *J. Am. Chem. Soc.*, 135(49), pp. 18629-18636 (2013).
Tang, et al., "Chirality-based Au@Ag Nanorod Dimers Sensor for Ultrasensitive PSA Detection," *ACS Appl. Mater. Interfaces*, 7 (23), pp. 12708-12712 (2015).
Zhu, et al., "A one-step homogeneous plasmonic circular dichroism detection of aqueous mercury ions using nucleic acid functionalized gold nanorods," *Chem. Commun.*, 48, pp. 11889-11891 (2012).

* cited by examiner

*Primary Examiner* — Sergio Coffa
(74) *Attorney, Agent, or Firm* — Foley & Lardner LLP

(57) ABSTRACT

Described herein are metal nanoparticle superstructures and methods and compounds for making the same.

24 Claims, 27 Drawing Sheets

FIGS. 16A-16D
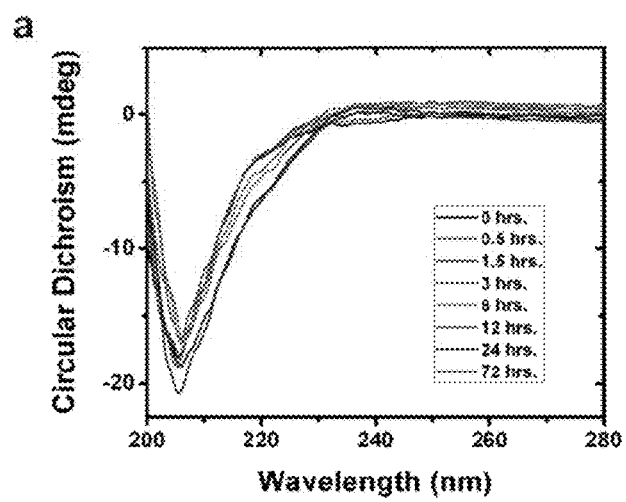
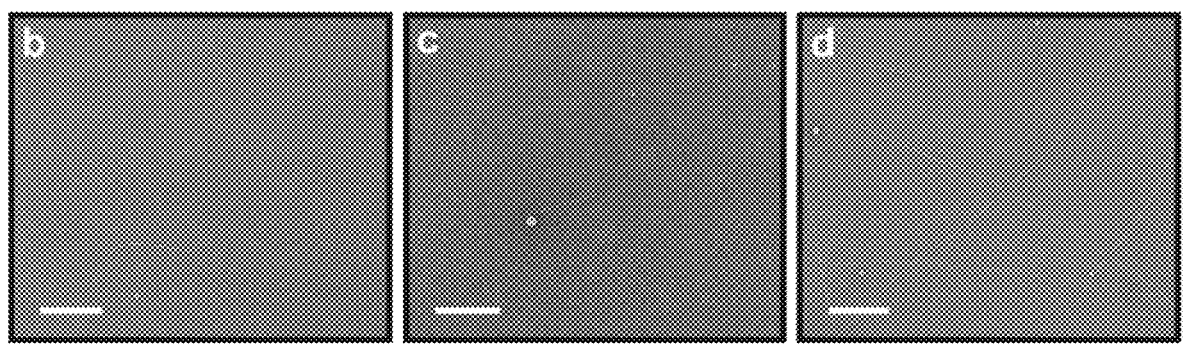

FIGS. 20A-20D
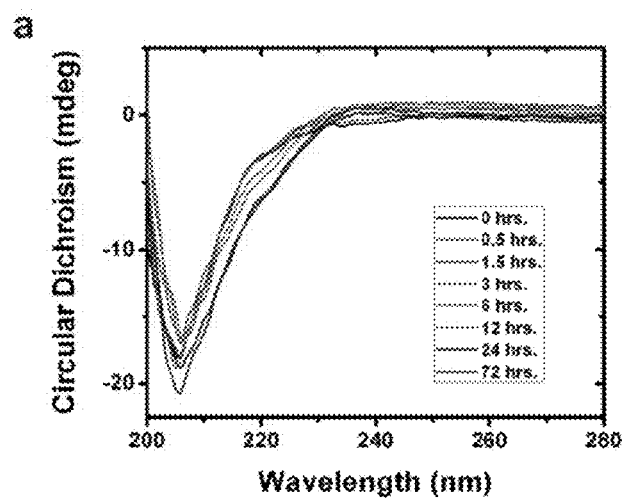
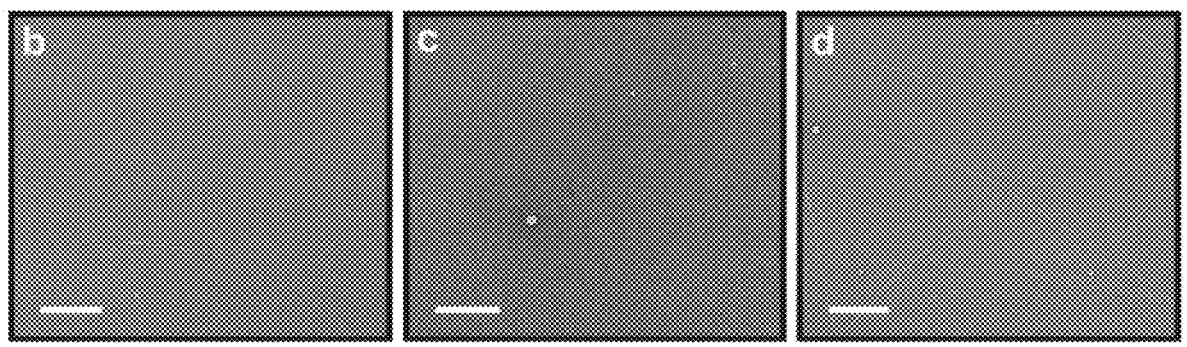

SINGLE-HELICAL GOLD NANOPARTICLE SUPERSTRUCTURES AND METHODS OF MAKING

CROSS-REFERENCE TO RELATED APPLICATION

This application claims the benefit of and priority to U.S. Application No. 62/435,487 filed Dec. 16, 2016, the contents of which is incorporated herein by reference in its entirety.

This invention was made with government support under National Science Foundation grant #DMR-0954380; and Air Force Office of Scientific Research grant #FA9550-11-1-0275. The government has certain rights in the invention.

BACKGROUND

Controlling the growth and assembly of nanoparticles is one of the most significant problems facing nanoscience. This is so in part because the size- and shape-dependent physicochemical and optoelectronic properties of metal and semiconductor nanoparticles are important factors in catalysis, biosensing, recording media, and optical devices.

Many templates, such as DNA, peptides, polymers or surfactants, dyes, and multidentate thioethers, have been used to control the growth and assembly of nanoparticles. These templates have received attention because they adsorb on the nanoparticle surface, preventing particle aggregation, and they change the surface properties of the resulting nanostructures, allowing for careful manipulation and assembly of the nanoparticles.

Chiral nanoparticle assemblies are an emerging class of materials. They have the potential to serve as nanoscale circular polarizers (Zhao et al., *Nat. Commun.*, 3:870 (2012); Gansel et al., *Science*, 325(5947):1513-1515 (2009)) chiroptical sensors (Tang et al., *Appl. Mater. Interfaces*, 7:12708-12712 (2015); Zhu et al., *Chem. Commun.*, 48:11889-11891 (2012; Wu et al., *Am. Chem. Soc.*, 135: 18629-18636 (2013)), and they represent an important new entry into the metamaterials catalogue.

Assembling nanoparticles into hierarchical materials however remains a considerable challenge. Simple processes are needed that can be employed to assemble nanoparticles into pre-designed designed functional materials. Without such processes, rational incorporation of nanoparticles into new materials remains largely infeasible.

SUMMARY

Some aspects of the present disclosure relate to a metal nanoparticle superstructure comprising a plurality of metal nanoparticles positioned in an essentially single helical assembly.

In some embodiments, the single helical assembly comprises a helical pitch of about 75 to about 115 nm. In some embodiments, an interparticle distance between metal nanoparticles in the metal nanoparticle superstructure are less than about 4 nm. In some embodiments, the metal nanoparticles have a length to width ratio of greater than 1. In some embodiments, the metal nanoparticles have a width of about 2 to about 16 nm and a length of about 8 to about 30 nm. In some embodiments, the plurality of metal nanoparticles comprise gold. In some embodiments, the plurality of metal nanoparticles comprise palladium or silver. In some embodiments, the metal nanoparticle superstructure is produced by contacting a metal or metal salt with a compound of the following formula I:

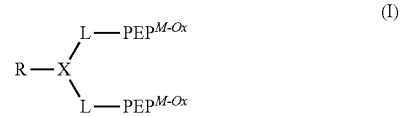

wherein R is a $C_6$-$C_{24}$ aliphatic or aromatic moiety; X is an optional N—($C_1$-$C_5$) amide, L is a linking moiety; and $PEP^{M-Ox}$ is a peptide having an affinity to the metal or metal salt, where at least one methionine residue is oxidized. In some embodiments, $PEP^{M-Ox}$ is AYSSGAPPM$^{ox}$PPF. In some embodiments, R is a $C_{14}$-$C_{20}$ aliphatic moiety.

Additional aspects of the present disclosure relate to a method for producing a metal nanoparticle superstructure comprising combining a metal or metal salt with a compound of the following formula I:

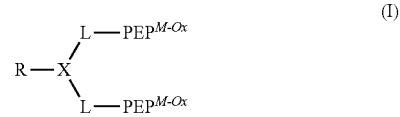

wherein R is a $C_6$-$C_{24}$ aliphatic or aromatic moiety; X is an optional N—($C_1$-$C_5$) amide L is a linking moiety; and $PEP^{M-Ox}$ is a peptide having an affinity to the metal or metal salt, where at least one methionine residue in the peptide is oxidized.

In some embodiments, the metal salt is used, and is a salt comprising gold, a salt comprising silver or a salt comprising palladium. In some embodiments, the metal or metal salt is combined with the compound of formula I in the presence of a buffering agent. In some embodiments, $PEP^{M-Ox}$ is AYSSGAPPM$^{ox}$PPF. In some embodiments, R is a $C_{14}$-$C_{20}$ aliphatic moiety. In some embodiments, the metal nanoparticle superstructure has a single helical assembly. In some embodiments, the compound of formula (I) has the structure:

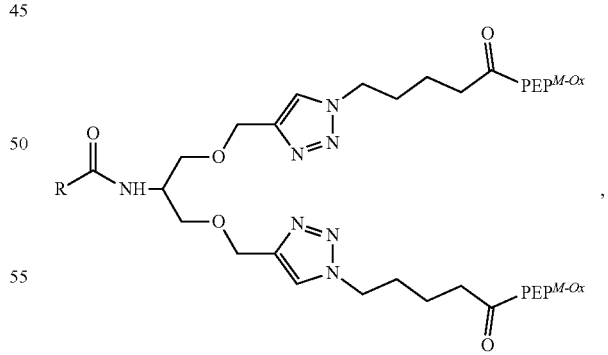

wherein R and $PEP^{M-Ox}$ are previously defined. In some embodiments, the single helical assembly comprises a helical pitch of about 75 to about 115 nm. In some embodiments, an interparticle distance between metal nanoparticles in the metal nanoparticle superstructure are less than 4 nm. In some embodiments, metal nanoparticles of the metal nanoparticle superstructure have a length to width ratio of greater than 1.

Additional aspects of the present disclosure relate to a compound of the following formula:

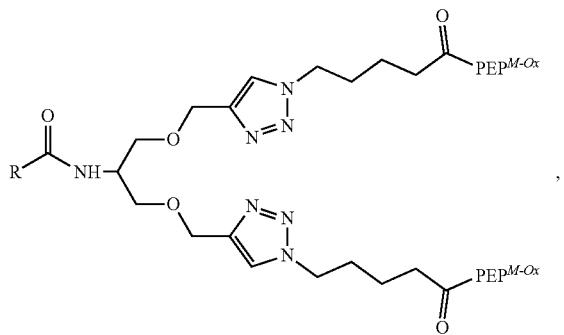

wherein R is a $C_6$-$C_{24}$ aliphatic or aromatic moiety; and $PEP^{M-Ox}$ is a peptide having an affinity to a metal or metal salt, where at least one methionine residue in the peptide is oxidized.

In some embodiments, $PEP^{M-Ox}$ is AYSSGAPPM$^{ox}$PPF. In some embodiments, the metal or metal salt comprises gold, silver, or palladium.

The foregoing general description and following brief description of the drawings and detailed description are exemplary and explanatory and not limiting of the disclosure.

BRIEF DESCRIPTION OF THE DRAWINGS

FIG. 2(A) double- and FIG. 2(B) single-helical nanoparticle superstructures from $C_{18}$-$(PEP_{Au})_2$ and $C_{18}$-$(PEP_{Au}^{M-Ox})_2$, respectively, under identical reaction conditions. $C_{18}$-$(PEP_{Au}^{M-Ox})_2$ was prepared via oxidation using $H_2O_2$.

FIGS. 3(a,b) TEM images of single-helical gold nanoparticle superstructures after 15 hours of reaction and FIG. 3(c) negative stained TEM image after 30 minutes of reaction. FIG. 3(d) The pitch of the helices, measured from TEM, is 94.4±6.6 nm (based on 80 counts). The Cryo-ET 3-D reconstruction of the single helices reveals their FIG. 3(e) left-handed helicity and, when viewed along the helix axis, their FIG. 3(f) core diameter where the fiber resides. FIG. 3(h) CD spectrum of the single-helical superstructures.

FIG. 4(c) Negative stained TEM image of $C_{18}$-$(PEP_{Au}^{M-Ox})_2$ fibers. FIG. 4(d) Fiber widths were 10.2±0.8 nm. FIG. 4(e) AFM reveals the helical ribbon morphology of $C_{18}$-$(PEP_{Au}^{M-Ox})_2$ fibers with a pitch of 96.2±4.8 nm and FIG. 4(f) a ribbon height of approximately 4 nm (height trace measured from the dashed line).

FIG. 6(a) Position of residue-specific 13C, 15N-labeling (arrows). FIG. 6(b) 2-D 13C-13C MAS ssNMR of labeled $C_{18}$-$(PEP_{Au}^{M-Ox})_2$ assemblies. Dashed and colored lines connect sets of peaks from labeled P10 (black dashed line) and A1 residues (solid lines). Three A1 conformations are marked with red (A1a), blue (A1b), and green (A1c) lines. FIG. 6(c) Secondary structure analysis of A1 ssNMR signals, showing A1a and A1b to be part of the $\hat{1}^2$-sheet core. FIG. 6(d) Secondary structure distribution in the three peptide conformers observed by ssNMR, along with their relative ssNMR peak intensities (right). FIG. 6(e) Amyloid core model based on a Class-3 steric zipper architecture. The compact Ala/Ser/Gly interface and the aromatic interface are attributed inter-sheet distances of ~6.5 Ã . . . and ~9 Ã . . . , respectively. Alternating peptides have distinct structures (blue/red coloring) that explain the observed peak doubling in the A1 $\hat{1}^2$-sheet peaks.

FIG. 7(a) Proposed assembly model of the helical ribbons. β-sheets run along the length of the fiber through H-bonding interactions (4.6 Å). The width of the ribbon, w, is determined by the number of stacked β-sheets with lamination spacings of ~6.5 and ~9 Å. PPII helices are exposed at the outer surface of the helical ribbon. FIG. 7(b) AFM (amplitude image) and FIG. 7(c) TEM image aligned to highlight the structural similarity between the fiber assembly and nanoparticle assembly, alongside FIG. 7(d) the proposed single-helix assembly model with gold particles bound to the outer face of the helical ribbon. The arrows show directionality similarities of the nanoparticle orientation.

FIG. 13(a) the helical pitch was 102.0±2.5 nm, based on 20 counts; FIG. 13(b) rotation angle was 34.3±4.9 degrees, based on 20 counts; and FIG. 13(c) inner diameter was 10.1±0.6 nm, based on 10 counts.

FIG. 14(a) CD spectrum of $PEP_{Au}^{M-Ox}$ capped gold nanoparticles and FIG. 14(b) their corresponding TEM image (scale bar=100 nm). Both single particles and particle aggregates are observed.

FIG. 15(a) TEM image of helices formed with 10 min. of sonication and 20 min. of incubation prior to HAuCl$_4$/TEAA addition. FIG. 15(b) The particle width and lengths were 12.1±3.0 nm and 23.9±3.9 nm, respectively (based on 75 counts, each). FIG. 15(c) CD spectrum of the optimized single helices exhibit a very strong CD signal. FIG. 15(d) UV-Vis extinction spectrum, and FIG. 15(e) g-factor graph showing absolute g-factor values up to 0.04. g-factor=$\Delta\varepsilon/\varepsilon$, where $\Delta\varepsilon$ is the molar circular dichroism and $\varepsilon$ is the molar extinctions.

FIGS. 16A-16D: FIG. 16(a) CD spectra of $C_{18}$-$(PEP_{Au}^{M-Ox})_2$ in 10 mM HEPES as a function of time. Negative stained TEM images after FIG. 16(b) 15 min., FIG. 16(c) 3 hrs., and FIG. 16(d) 72 hrs. are shown (scale bar=500 nm). Under these conditions, fibers form very slowly, and very few fibers are observed at early time points.

FIG. 19(a) CD spectrum of $C_{18}$-$(PEP_{Au}^{M-Ox})_2$ in 10 mM HEPES and 1 mM $CaCl_2$ after one day, and FIG. 19(b) corresponding negative stained TEM image (scale bar=500 nm).

FIGS. 20A-20D: FIG. 20(a) CD spectra of $C_{18}$-$(PEP_{Au}^{M-Ox})_2$ in 10 mM HEPES as a function of time. Negative stained TEM images after FIG. 20(b) 15 min., FIG. 20(c) 3 hrs., and FIG. 20(d) 72 hrs. are shown (scale bar=500 nm). Under these conditions, fibers form very slowly, and very few fibers are observed at early time points.

FIG. 21(a) Integrated d-spacings of the XRD diffractogram. FIG. 21(b) Figure showing the off-diagonal planes and the d-spacing between these planes, accounting for the off-meridian reflections with a d-spacing of 4.2 Å. FIG. 21(c) Figure showing the strand-to-strand and sheet-to-sheet distances as revealed via XRD.

FIG. 22(a) Aliphatic $^{13}C$ 1D MAS ssNMR spectrum of the site-specifically labeled $C_{18}$-$(PEP_{Au}^{M-Ox})_2$ assemblies (top), with the P10 peaks indicated. Bottom: ssNMR spectrum of fibrillar huntingtin exonl-derived peptide htt$^{NT}Q_{30}P_{10}K_2$, with $^{13}C$, $^{15}N$-labeled Pro P48. In both cases the labeled Pro is part of a PPII helix that flanks the β-sheet amyloid core. FIG. 22(b) Long-mixing 500 ms PDSD 2D ssNMR spectrum on the labeled $C_{18}$-$(PEP_{Au}^{M-Ox})_2$ assemblies. Compared to the short-mixing spectrum (FIG. 6b) only new intra-residue P10 peaks are observed, with no contacts between the distinct A1 conformers. FIG. 22(c) Compact zipper interfaces mediated by Ser and other small amino acids in amyloid-like crystals of peptides SSTSAA and SSTNVG from RNase and IAPP. The compact 6 Å inter-sheet distance is indicated. FIG. 22(d) Tyr ring stacking in GNNQQNY in-register parallel (IP) β-sheets. FIG. 22(e) Amyloid interfaces featuring aromatic residues generate wider 9-10 Å inter-sheet distances. Illustrated for Phe in this Class-2 amyloid-like crystal of peptide ANFLVH. The PDB entries for the four peptide crystal structures are 2ONW, 3DG1, 1YJP, and 5E5X.

FIG. 24(q) Average helical pitch and nanoparticle length and width, tabulated as a function of peptide conjugate tail length.

DETAILED DESCRIPTION

Figures 1A, 1B:
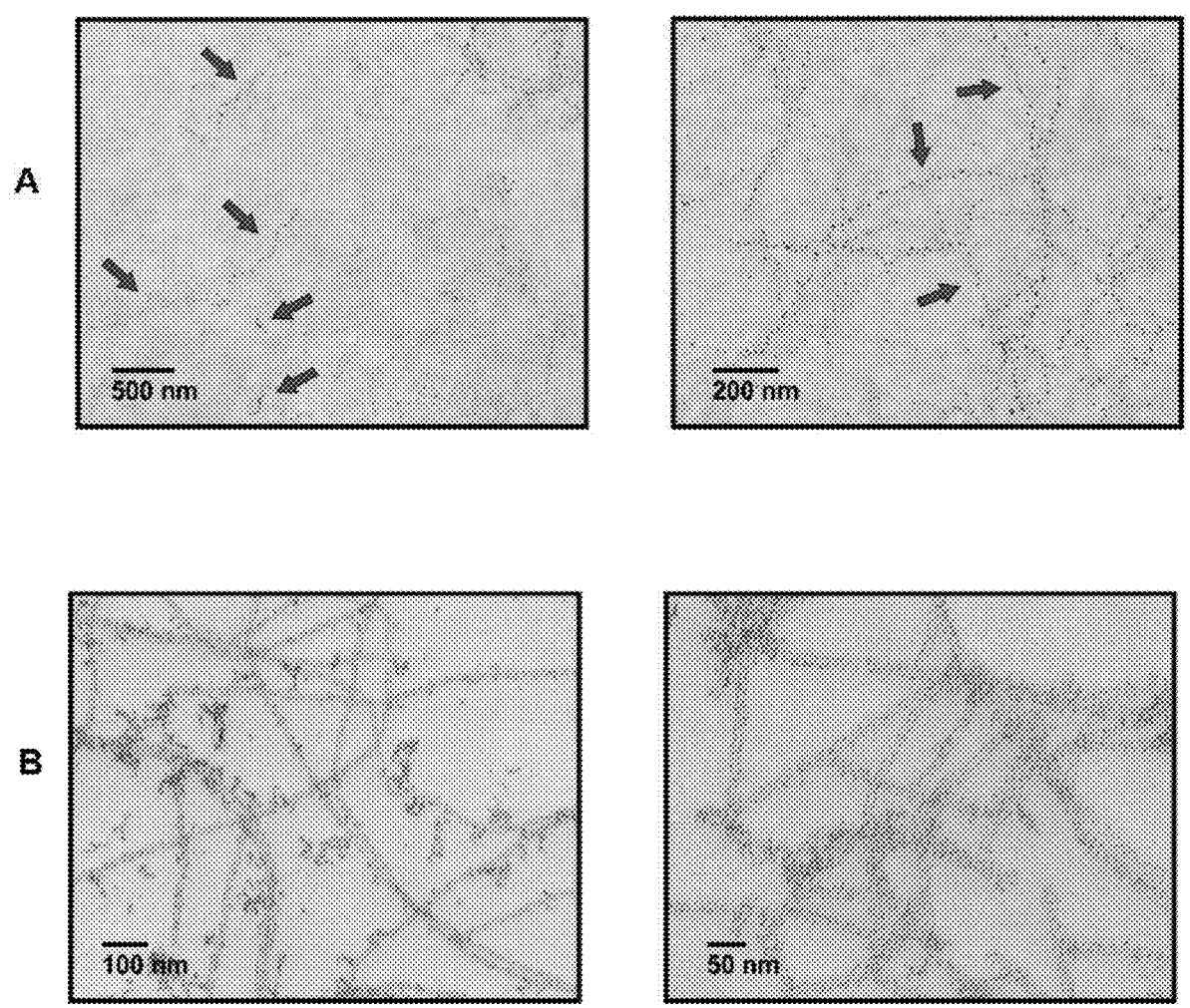
FIG. 1A shows transmission electron microscopy (TEM) images of metal nanoparticle superstructures comprising a plurality of silver nanoparticles according to an aspect of the disclosure. The arrows reveal the helicity of the nanoparticle superstructures.
FIG. 1B shows TEM images of metal nanoparticle superstructure comprising a plurality of palladium nanoparticles according to an aspect of the disclosure.

Peptides, which can assemble into chiral architectures, are attractive molecular building blocks that can be used to direct the assembly of nanoparticles into chiral superstructures. Described herein is the discovery of peptide-based nanoparticle assembly methods, where tailored peptide conjugate molecules are used to direct the assembly of nanoparticles. In a model system, the methods have been used to assemble gold nanoparticles into double-helical arrays having tailorable structures and chiroptical properties. Gold is used as an exemplary metal in the examples, but other metals can be used in the methods of the invention as described herein.

As detailed in the example below, the metal-peptide binding conjugate molecules play a dual role in this methodology: they bind to metal nanoparticle surfaces during particle synthesis and they direct their assembly (e.g., gold-binding peptide conjugate molecules, R-$PEP_{Au}$ (R=organic tail; $PEP_A$=AYSSGAPPMPPF)).

Thus, detailed herein is the preparation of unique metal nanoparticle single helices that exhibit exceptionally strong plasmonic chiroptical activity. The underlying molecular basis of these superstructures was examined to arrive at a structural model that thoroughly accounts for their assembly and provides the basis for the rational construction of chiral nanoparticle superstructures.

In particular, the Examples below demonstrate that a metal-peptide conjugate (e.g., $C_{18}$-$(PEP_{Au}^{M-oX})_2$) directs the formation of well-defined single-helical metal nanoparticle assemblies having strong plasmonic chiroptical activity that ranks among the highest observed for comparable systems. In addition, a molecular assembly model is detailed based on data acquired from several characterization techniques that is consistent with the structural parameters of the single helices. This model details how peptide conjugate molecules constructed from inorganic-binding peptides can simultaneously self-assemble and bind to inorganic nanoparticles, thus enabling the assembly of nanoparticles into intricate superstructures.

Metal Nanostructures

Provided herein, in one aspect, are metal nanoparticle superstructures. In some embodiments, the metal nanoparticle superstructures comprise a plurality of metal nanoparticles. These nanostructures may comprise one or more metals, such as a transition metal (e.g., scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, rutherfordium, dubnium, seaborgium, bohrium, hassium, meitnerium, unumnilium, unununium, or ununbium). In some embodiments, the metal nanostructure comprises an alloy of two or more metals, or a metal salt, or a metal oxide. Exemplary embodiments include gold, silver, platinum, iron oxide, zinc sulfide, cadmium sulfide, cobalt, aluminum, copper selenide, titanium nitride, and palladium.

Some metal nanoparticle superstructures of the present disclosure may have a single-helical form. For example, the single helical assembly comprises a helical pitch of about 60 to about 130 nm, or about 75 to about 115 nm, or about 75, about 80, about 85, about 90, about 95, about 100, about 105, about 110 or about 115 nm.

Some metal nanoparticle superstructures of the present disclosure may be comprised of nanoparticles, wherein the interparticle distance between metal nanoparticles in the metal nanoparticle superstructure are less than or equal to about 6, less than or equal to about 5, less than or equal to about 4, less than or equal to about 3, less than or equal to about 2, or less than or equal to about 1 nm. In some embodiments, the metal nanoparticles have a length to width ratio of greater than about 1. In some embodiments, the metal nanoparticles have a width of about 2 to about 16 nm (e.g., about 2, about 3, about 4, about 5, about 6, about 7, about 8, about 9, about 10, about 11, about 12, about 13, about 14, about 15, or about 16 nm) and a length of about 8 to about 30 nm (e.g., about 8, about 9, about 10, about 11, about 12, about 13, about 14, about 15, about 16, about 17, about 18, about 19, about 20, about 21, about 22, about 23, about 24, about 25, about 26, about 27, about 28, about 29 or about 30 nm).

Some metal nanoparticle superstructures of the present disclosure demonstrate chiroptical activity, e.g., of the of the single helices. In some embodiments, the nanoparticle superstructures have an anisotropy factor (g) of up to about 0.04 (e.g., up to about 0.01, up to about 0.02, up to about 0.03, or up to about 0.04).

Method of Making Metal Nanostructures

In some embodiments, the metal nanoparticle superstructures of the present disclosure combine a metal or metal salt with a compound of the following formula I:

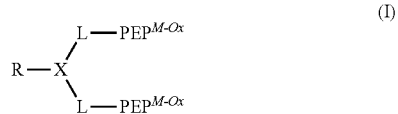

wherein R is a $C_6$-$C_{24}$ aliphatic or aromatic moiety;

X is an optional N—($C_1$-$C_5$) amide;

L is a linking moiety; and $PEP^{M-Ox}$ is a peptide having an affinity to the metal or metal salt, where at least one methionine residue in the peptide is oxidized.

In some embodiments, the R moiety may be a $C_6$, $C_8$, $C_{10}$, $C_{12}$, $C_{14}$, $C_{16}$, $C_{18}$, $C_{20}$, $C_{22}$, or $C_{24}$ aliphatic carbon chain that is linear or branched. In some embodiments, the R moiety includes a $C_6$-$C_{24}$ moiety comprising aliphatic and aromatic carbons, such as a linear or branched aliphatic chain and an aromatic phenyl or napthyl moiety.

In some embodiments, the linking moiety comprises about 5 to about 20 atoms in the backbone connecting the R or X moiety to the peptide. For example, the following linking moiety includes 11 atoms in the backbone connecting the R or X moiety to the peptide:

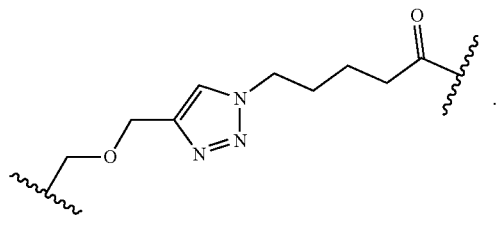 [SMILES: *COCc1cn(CCCCC(*)=O)nn1]

The linking moiety may comprise about 5 to about 30 atoms, and may include aliphatic, aromatic, heteroaromatic moieties as well as heteroatoms, such as N, S, O.

$PEP^{M-Ox}$ is a peptide having an affinity to a metal or metal salt, where at least one methionine residue in the peptide is oxidized. In some embodiments, the $PEP^{M-Ox}$ moiety comprises about 5 to about 20 peptide residues, for example, about 5, about 6, about 7, about 8, about 9, about 10, about 11, about 12, about 13, about 14, about 15, about 16, about 17, about 18, about 19, or about 20 residues. Various unoxidized peptides having an affinity to a metal or metal salt are known in the art, and their oxidized versions are intended to be within the present disclosure, for example, the oxidized versions of AYSSGAPPMPPF. In other embodiments, the "$PEP^{M-Ox}$" of Formula I can be $PEP^M$, a peptide having an affinity to the metal or metal salt, where methionine residues in the peptide are not oxidized.

In some embodiments, the metal or metal salt is combined with the compound of formula I in the presence of a buffering agent. Examples of buffering agents include those that can maintain a physiological pH, such as a phosphate buffer, an acetate buffer, a citrate buffer, a sodium phosphate buffer, a potassium phosphate buffer, or a sodium acetate buffer. For example, hydrogen buffers which are N-substituted amino acids compatible with common biological media, 4-(2-hydroxyethyl)-1-piperazineethanesulfonic acid (HEPES), triethylammonium acetate (TEAA), N-cyclohexyl-3-aminopropanesulfonic acid (CAPS), 3-(Cyclohexylamino)-2-hydroxy-1-propanesulfonic acid (CAPSO), N,N-Bis(2-hydroxyethyl)-2-aminoethanesulfonic acid (BES), N-(2-Acetamido)-2-aminoethanesulfonic acid (ACES), N-Cyclohexyl-2-aminoethanesulfonic acid (CHES), Tricine (N-(Tri(hydroxymethyl) methyl)glycine), TES buffer (2-[[1, 3-dihydroxy-2-(hydroxymethyl)propan-2-yl]amino]ethanesulfonic acid), ADA buffer (N-(2-Acetamido)iminodiacetic acid), 3-[4-(2-Hydroxyethyl)-1-piperazinyl]propanesulfonic acid (HEPPS or EPPS buffer), P-Hydroxy-4-morpholinepropanesulfonic acid (MOPSO), 3-(N-morpholino)propanesulfonic acid (MOPS), 4-(N-Morpholino)butanesulfonic acid (MOBS), and N-(2-Hydroxyethyl)piperazine-N'-(4-butanesulfonic acid) (HEPBS). In some embodiments, the metal or metal salt is combined with the compound of formula I in the presence of two or more buffering agents. An exemplary physiological pH is from about 6.5 to about 9, or about 7 to about 9. In some embodiments, a physiological pH is that found in blood and plasma.

In some embodiments, the conditions include aqueous conditions, presence of appropriate metal salt, and a reducing agent (e.g. $NaBH_4$). Synthetic conditions may be tailored depending on the nanoparticle composition targeted, as would be understood by the skilled artisan.

Detailed Analysis of the Experimental Data

Figure 8A:
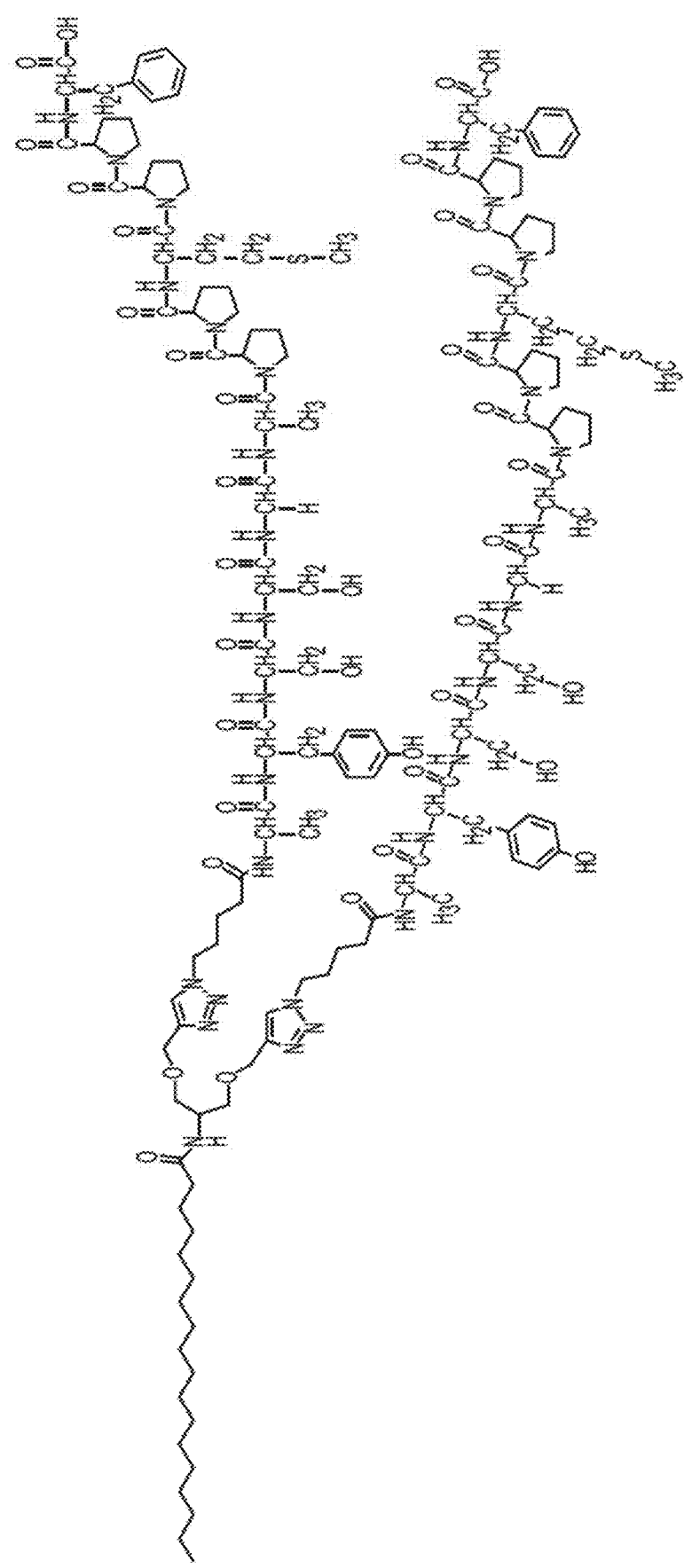
FIGS. 8A-8B: chemical structure of FIG. 8(a) C18-$(PEP_{Au})_2$ and FIG. 8(b) C18-$(PEP_{Au}^{M-Ox})_2$.
Figure 8B:
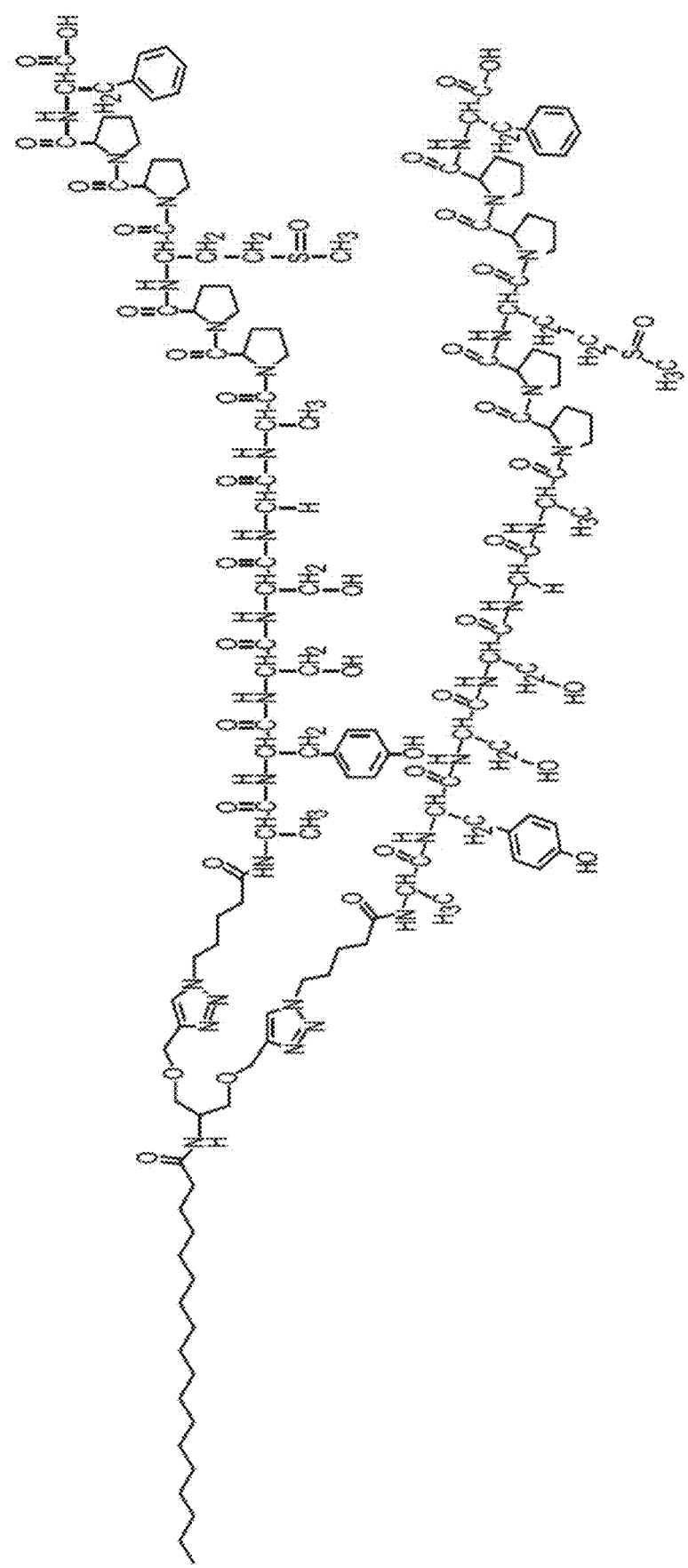
Figures 9A, 9B:
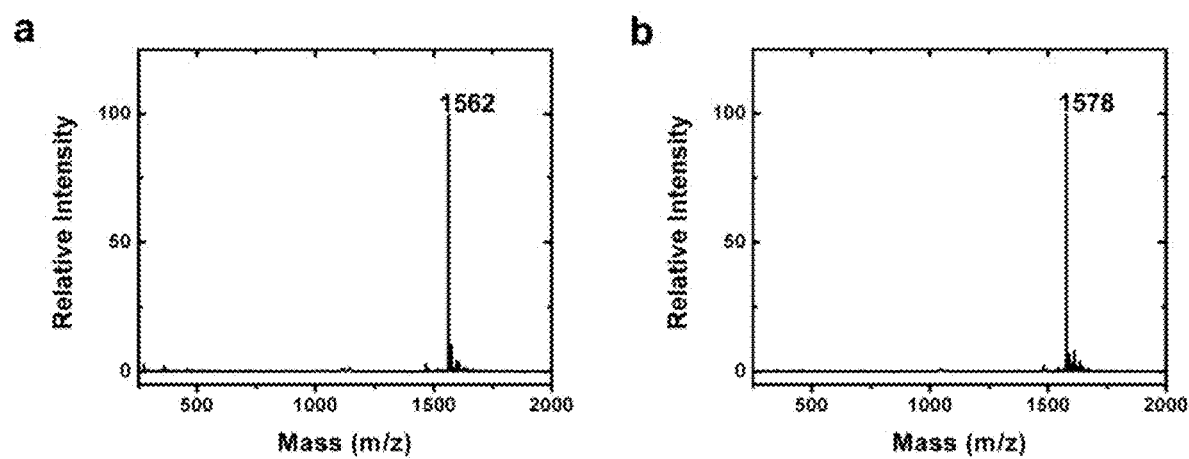
FIGS. 9A-9B: LCMS spectra of FIG. 9(a) C18-$(PEP_{Au})_2$, m/z=1562 (m/2) and FIG. 9(b) C18-$(PEP_A^{M-Ox})_2$, m/z=1578 (m/2).
Figure 10:
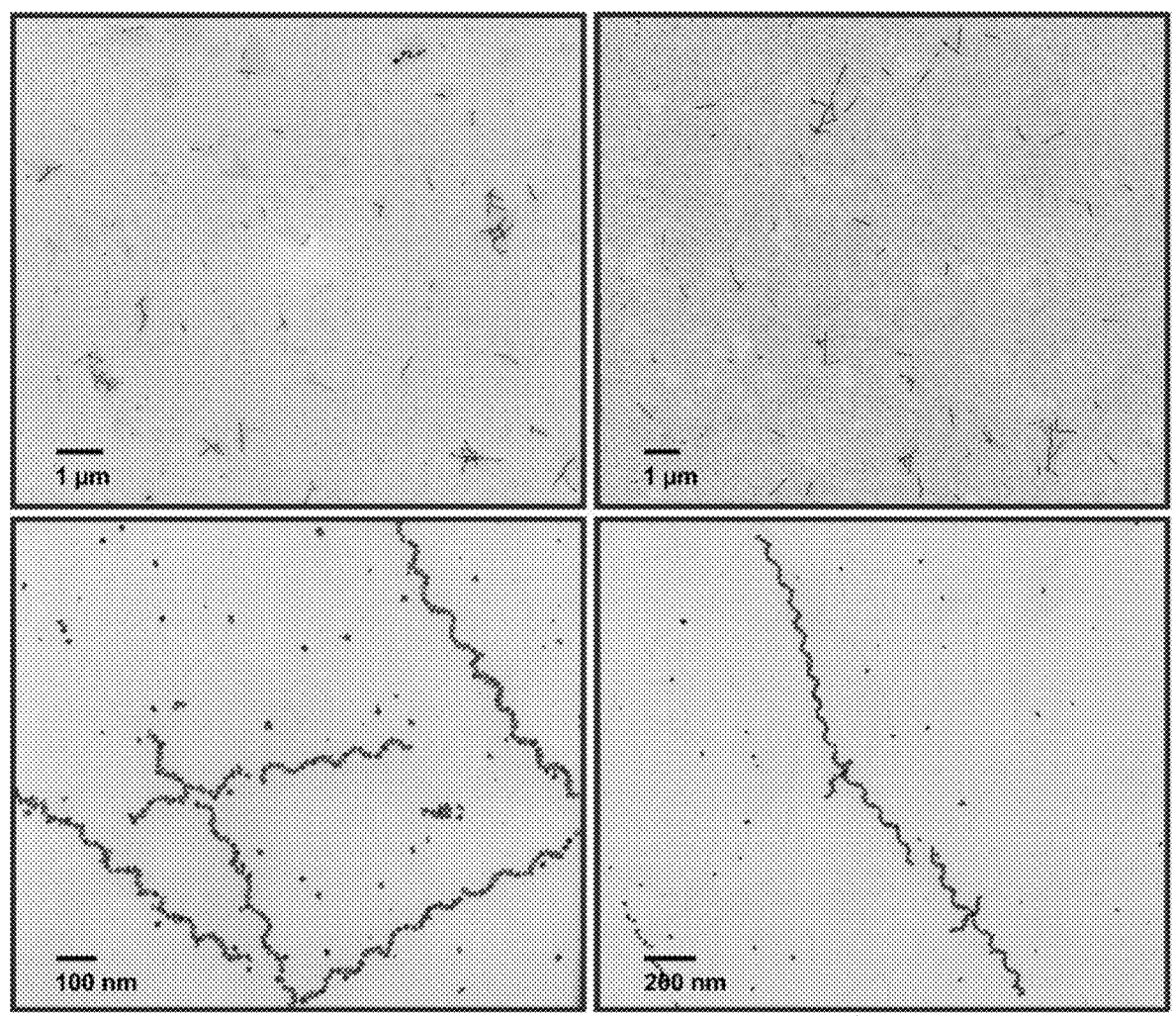
FIG. 10: TEM images of the single-helical superstructure at different magnifications.

Single Helix Synthesis and Chiroptical Properties. The inventors proposed that oxidation of the divalent peptide conjugate $C_{18}$-$(PEP_{Au})_2$ (FIG. 8a) to $C_{18}$-$(PEP_{Au}^{M-Ox})_2$ (PEP$_{Au}^{M-Ox}$=AYSSGAPPM$^{ox}$PPF) results in the formation of single-helical superstructures. To test this hypothesis, $C_{18}$-$(PEP_{Au})_2$ was chemically oxidized; LCMS data for these oxidized conjugates confirmed the increase in molecular weight associated with the addition of two oxygens (FIG. 9). The oxidized conjugates exclusively directed the assembly of single-helical gold nanoparticle superstructures.

Figures 3A, 3B, 3C, 3D, 3E, 3F, 3G:
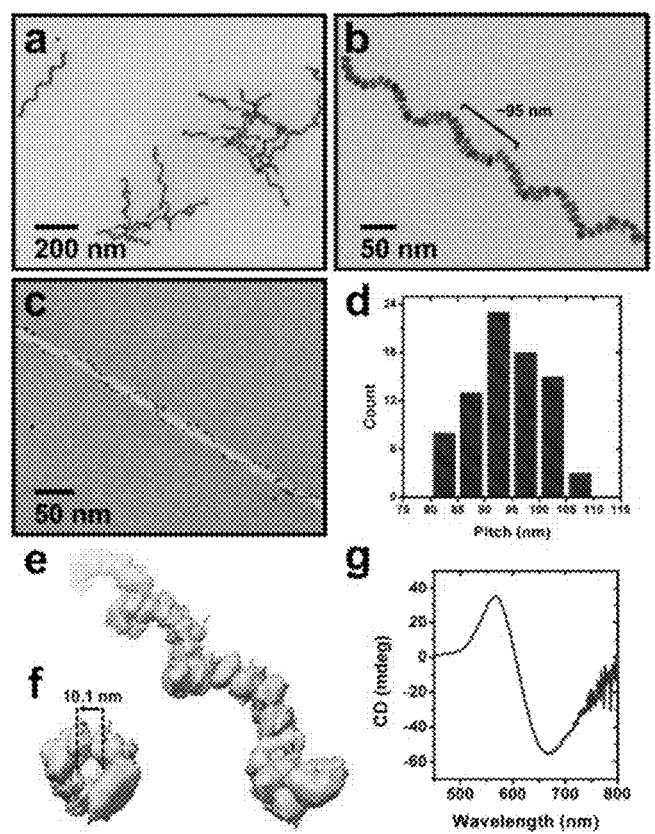
FIGS. 3A-3G shows Single helix characterization.
Figure 11:
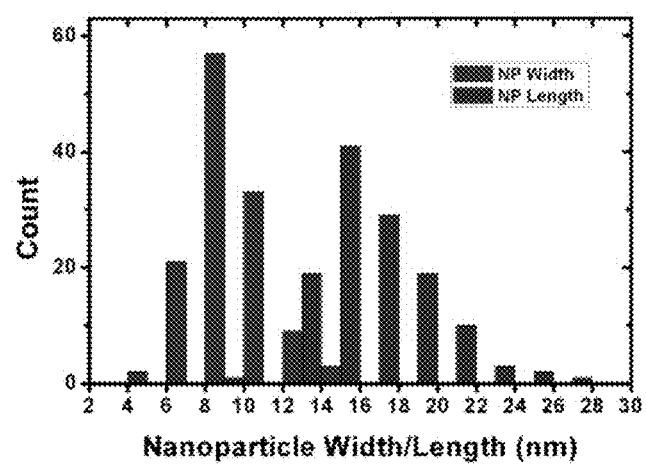
FIG. 11: The nanoparticle length and widths of the single-helical superstructure were 16.6±3.0 nm and 9.6±1.9 nm, respectively, after 15 hours of reaction (based on 125 counts each).
Figures 12A, 12B, 12C, 12D, 12E, 12F:
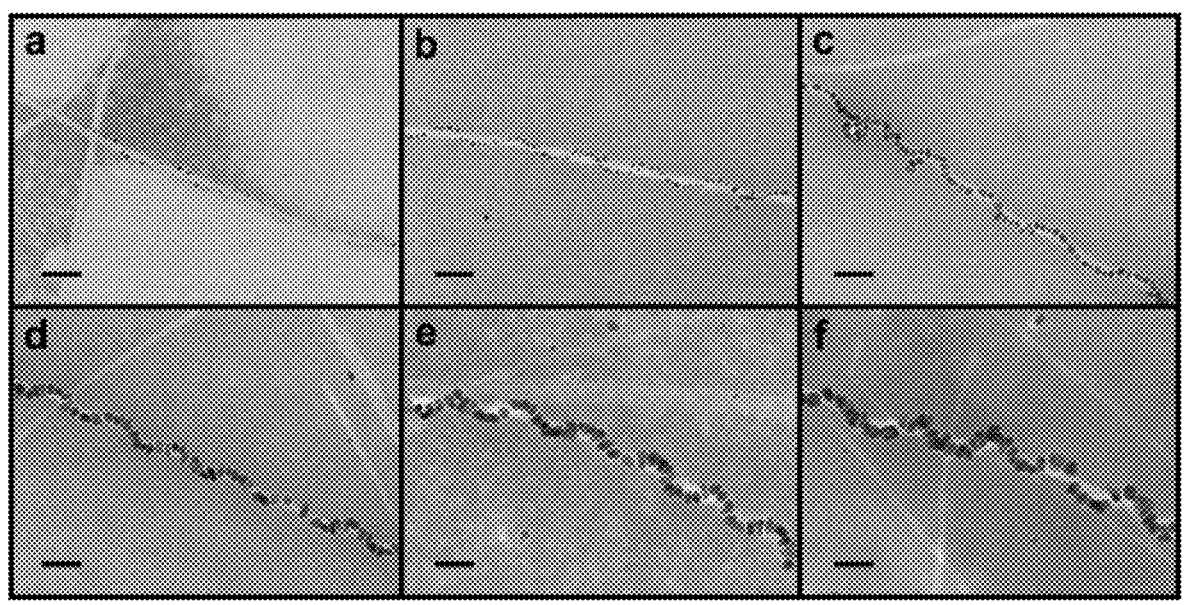
FIGS. 12A-12F: Negative stained TEM images of the single helices after FIG. 12(a) 0 min., FIG. 12(b) 30 min., FIG. 12(c) 2 hrs., FIG. 12(d) 5 hrs., FIG. 12(e) 8 hrs., and FIG. 12(f) 2 days of reaction at room temperature (scale bar=50 nm).
Figures 13A, 13B, 13C:
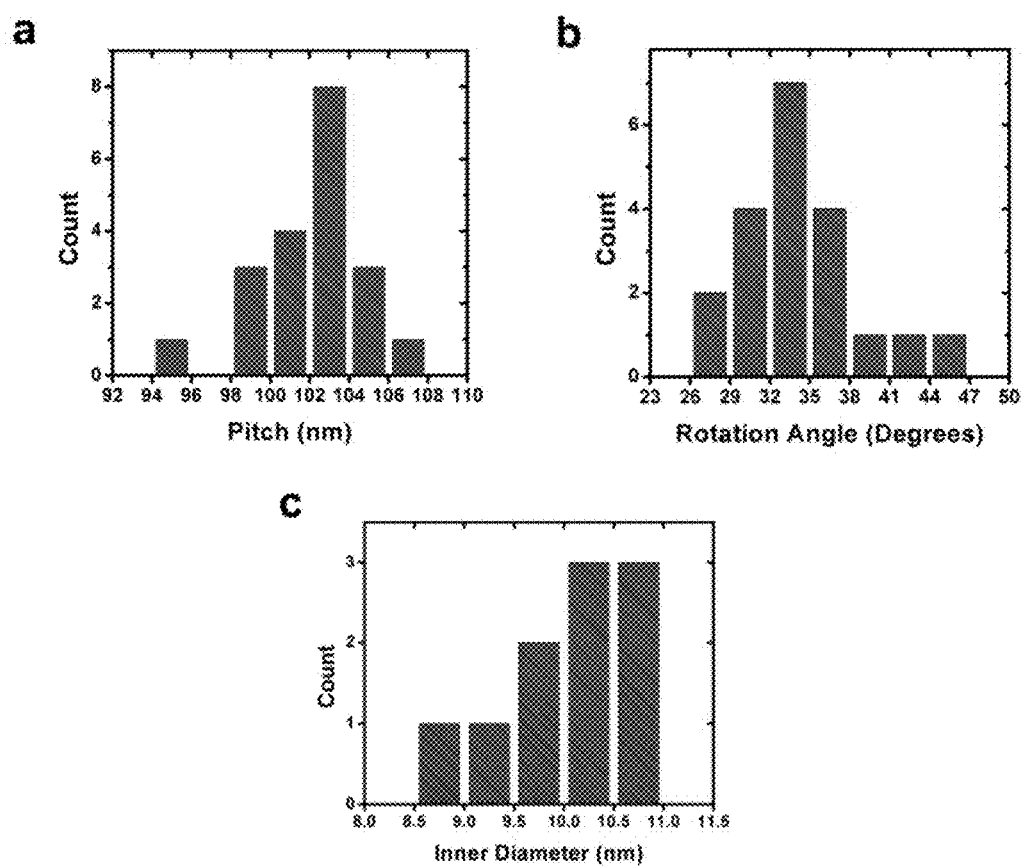
FIGS. 13A-13C: structural parameters of single helices from cryo-ET.

Next, single-helical gold nanoparticle Assemblies were characterized. Transmission electron microscopy (TEM) images (FIGS. 3a-c and 10) revealed that the single helices have an average pitch of 94.4±6.6 nm (FIG. 3d) and are composed of individual rod-like nanoparticles with lengths of 16.6±3.0 nm and widths of 9.6±1.9 nm (FIG. 11). At early stages of the synthesis and assembly process, the nanoparticles are spherical, but over time they grow into oblong rod-like nanoparticles (FIG. 12). Negative stained TEM grids indicate that the particles assemble along 1-D $C_{18}$-$(PEP_{Au}^{M-ox})_2$-based fibers (FIG. 3c). Cryogenic-electron tomography (cryo-ET) was employed (FIG. 3e, f) to determine the 3-D architecture of the 1-D assemblies. The reconstructed tomographic volume confirms that the helices are left-handed, which can be attributed to L amino acid residues comprising the peptides. Structural parameters were also gathered from the 3-D reconstruction of the helices. The pitch was found to be 102.0±2.5 nm, within error of the measured data from 2-D TEM images, and the rotation angle per particle was 34.3±4.9 degrees, corresponding to approximately 10-11 nanoparticles per pitch length (FIGS. 13a, b). The inner diameter of the helical superstructure was 10.1±0.6 nm (FIGS. 3e and 13c). This distance corresponds to the measured width of the fibers.

Figures 14A, 14B:
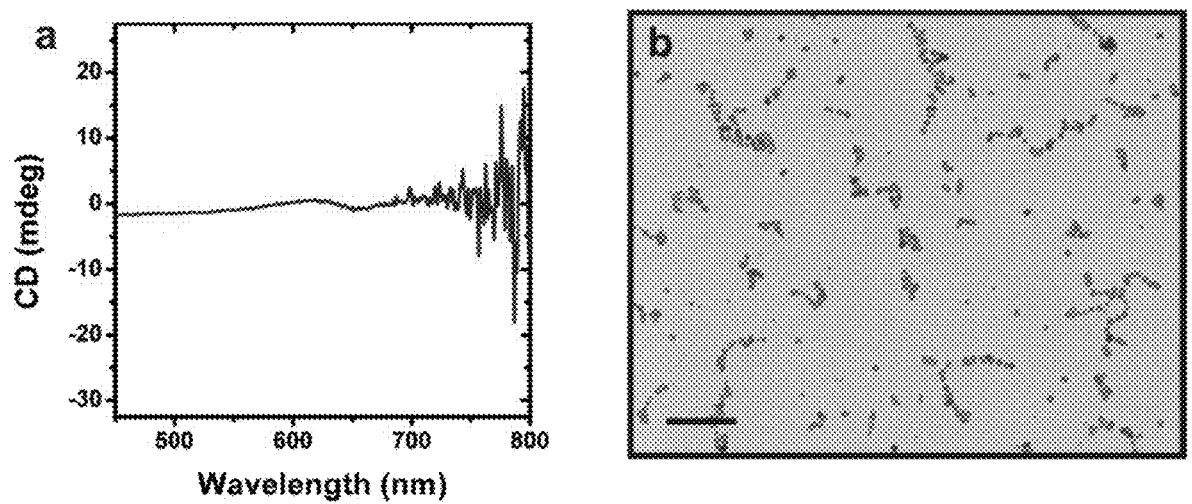
FIGS. 14A-14B.
Figures 15A, 15B, 15C, 15D, 15E:
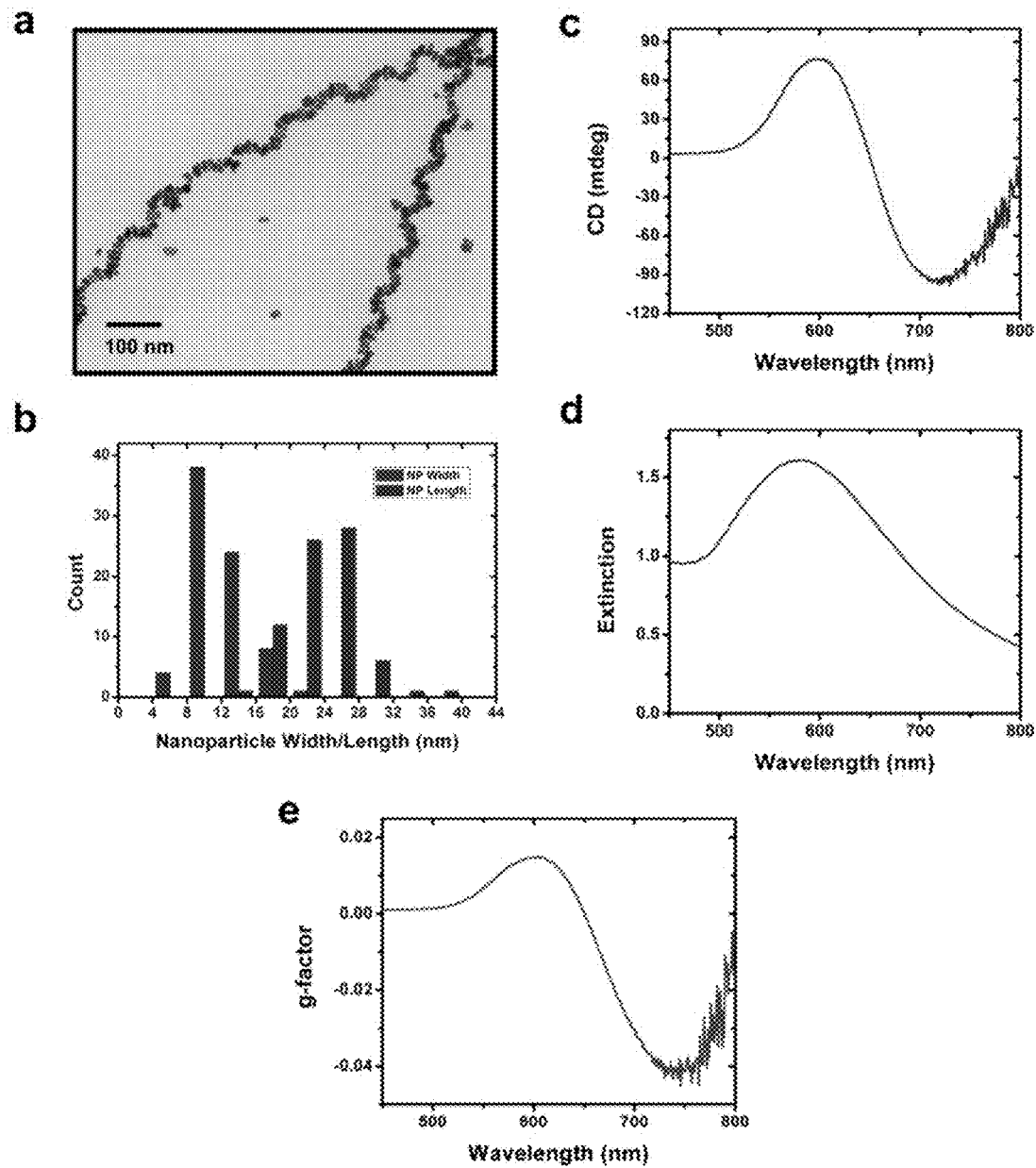
FIGS. 15A-15E.

Circular dichroism (CD) spectroscopy was used to characterize the chiroptical activity of the single helices. The single helices exhibit a strong bisignate peak centered at approximately 600 nm, near the collective plasmonic extinction band for the assemblies (FIG. 3g). Gold nanoparticles capped with $PEP_{Au}^{M-Ox}$, showed only a weak CD signal (FIG. 14). Therefore, it was concluded that the strong plasmonic CD signal for the single helices originates from the chiral helical arrangement of metal (i.e., gold) particles. It is important to compare the chiroptical activity of the single helices to other reported chiral nanoparticle assemblies. The anisotropy factor, g, is typically used as a benchmark value for determining the intensity of the chiroptical signal. Optimized assemblies (FIGS. 15a, b), for which synthetic conditions were tuned to increase particle dimensions, have an absolute g-factor up to ~0.04 (FIG. 15e), which is one of the highest reported to date for comparable nanoparticle assemblies.

Peptide Conjugate Assembly Studies. The single helices' intense chiroptical activity prompted examination of the assembly and structure of $C_{18}$-$(PEP_{Au}^{M-ox})_2$. Understanding the underlying molecular structure of the fibers and how it correlates to the final nanoparticle assembly allows for rational design of peptide conjugate building blocks and precise control over nanoparticle superstructure assembly and properties.

Figures 4A, 4B, 4C, 4D, 4E, 4F:
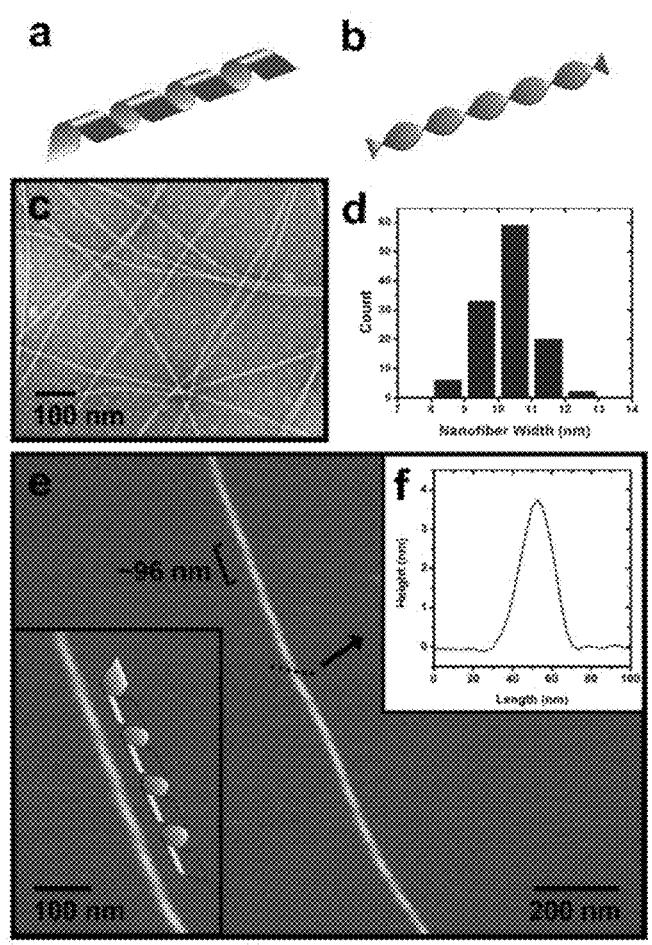
FIGS. 4A-4F: $C_{18}$-$(PEP_{Au}^{M-Ox})_2$ fiber morphology studies. Helical peptide amphiphile fibers typically exhibit either FIG. 4(a) helical ribbon or FIG. 4(b) twisted ribbon morphology.

The morphology of the $C_{18}$-$(PEP_{Au}^{M-ox})_2$ fibers in the absence of gold nanoparticles was studied. Acylated peptide amphiphiles are known to assemble into two principal helical morphologies: twisted ribbons and helical ribbons (FIGS. 4a, b). Both assemblies are defined by a cross-β amyloid-like structure. Twisted ribbons are characterized by their saddle-like curvature with a C2 symmetry axis and both ribbon faces equally exposed. Helical ribbons, in contrast, have cylindrical curvature and one face of the ribbon is directed toward the interior of the helical coil and the other is directed to the exterior. In both cases, the helicity originates from the chirality of the peptide-based molecular building blocks. The observed single helix architecture suggests that $C_{18}$-$(PEP_{Au}^{M-ox})_2$ fibers assemble into helical ribbons, and the gold nanoparticles decorate the exterior face of the helical ribbon. It is believed that the twisted ribbon morphology favors the formation of a double-helical superstructure, where the particles associate to either both edges or both faces of the ribbon.

To precisely determine the fiber morphology, samples were analyzed using numerous microscopy techniques. TEM verified the presence of 1-D fibers, in addition to small pseudospherical aggregates, which are always present in varying amounts, depending on the length of time allowed for assembly process. The fiber widths, measured via TEM, were 10.2±0.8 nm, which is consistent with the cryo-ET data that defined the inner diameter of the nanoparticle superstructure to be approximately 10.1 nm (FIG. 4d). Distinct morphological features of the fibers, such as their helicity, were indistinguishable using traditional TEM imaging. Tapping-mode atomic force microscopy (AFM) images clearly revealed that the fibers adopt the helical ribbon morphology (FIG. 4e). The pitch, measured via AFM, was 96.2±4.8 nm, consistent with the pitch of the gold nanoparticle single helices. The vertical thickness of the ribbon was ~4 nm (FIG. 4f). Height traces suggest that the coiled helical ribbon compresses onto the mica substrate, which is not surprising as such compression/collapse is common for soft assemblies having a hollow interior. The morphological similarities between the helical ribbons and the metal (i.e., gold) nanoparticle single helices imply similarities between $C_{18}$-$(PEP_{Au}^{M-ox})_2$ assembly in both the presence and absence of gold nanoparticles. These observations suggest that the geometry and structure of the peptide conjugate assembly directs the metal (i.e., gold) particle assembly.

Next, the internal structure within the $C_{18}$-$(PEP_{Au}^{M-ox})_2$ fibers was examined. An amide I absorption peak at 1630 cm−1, characteristic of parallel β-sheet secondary structure, was observed in the Fourier transform infrared (FTIR) spectrum. In addition, a peak at 2922 cm−1 corresponding to CH stretches was observed, signifying relatively ordered packing of the alkyl chains within the assembly. CD spectra for $C_{18}$-$(PEP_{Au}^{M-ox})_2$ were collected under conditions that promote fiber assembly. A prominent negative band centered at ~211 nm and a positive band centered at ~238 nm were observed. Negative peaks corresponding to the presence of β-sheetstructure are typically observed around 215-220 nm for peptide amphiphile assemblies. Molecular simulation studies of PEPAu predict that the proline residues near the C-termini adopt a polyproline II (PPII) conformation when free in solution. PPII helices typically display a strong negative CD band at ~205 nm. A negative band was observed at 205 nm for $C_{18}$-$(PEP_{Au}^{M-ox})_2$ under conditions that do not promote fiber assembly (i.e., no β-sheet formation). Therefore, it was concluded that the observed signal in the CD spectrum of $C_{18}$-$(PEP_{Au}^{M-ox})_2$ fibers was a superposition of bands deriving from both β-sheet and PPII secondary structure in the assembled fibers.

Figure 5:
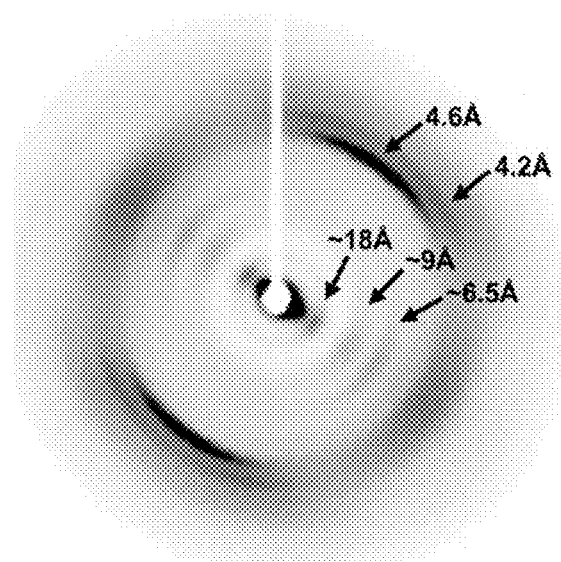
FIG. 5: X-ray diffractogram. 2-D X-ray diffraction pattern of aligned $C_{18}$-$(PEP_{Au}^{M-Ox})_2$ fibers reveal cross-β architecture. Meridional (4.6 Å), off-meridional (4.2 Å), and equatorial reflections (~18 Å, ~9 Å, and ~6.5 Å) are labeled.
Figures 21A, 21B, 21C:
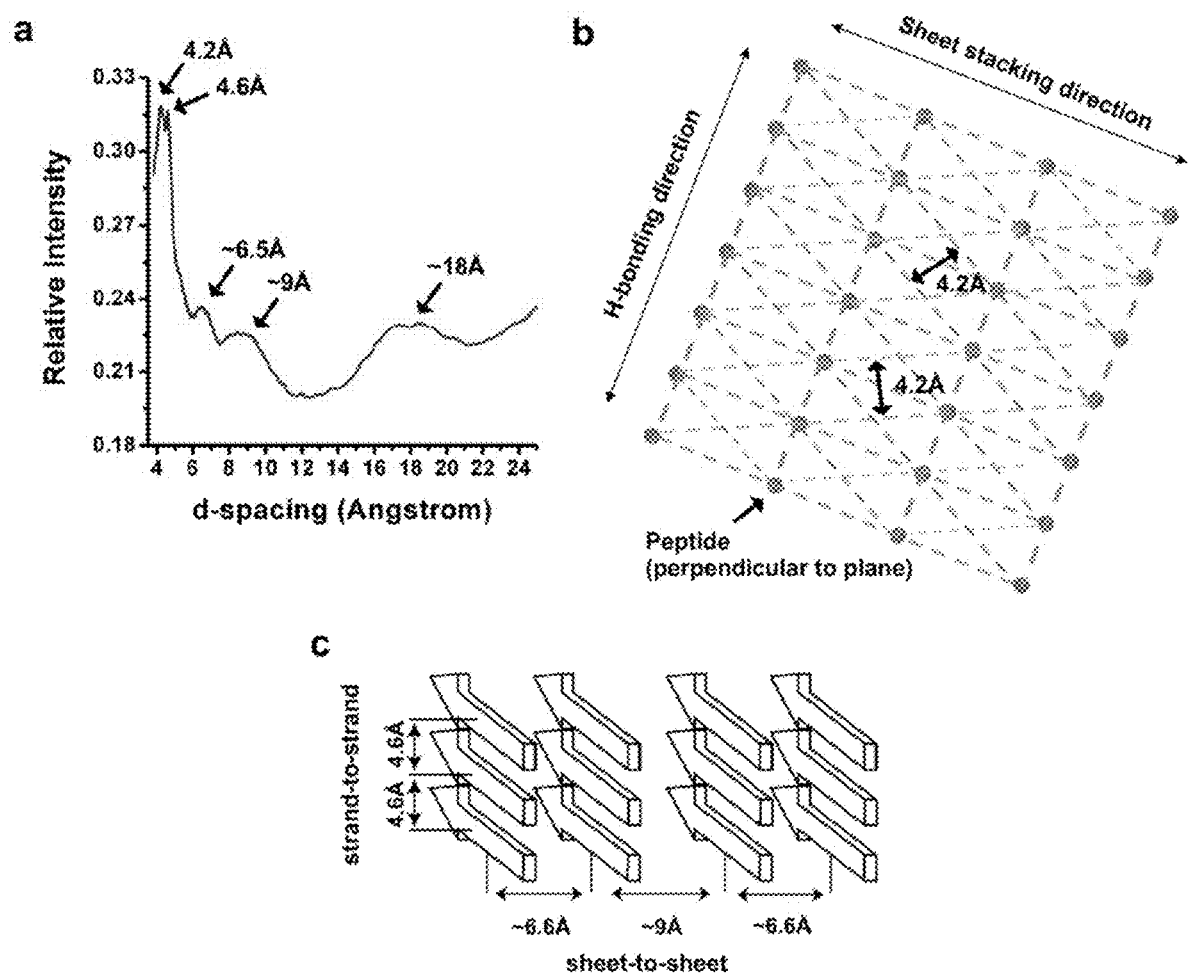
FIGS. 21A-21C.

While CD and FTIR spectroscopy provided information about the secondary structure, X-ray diffraction (XRD) experiments were conducted to probe the molecular-level packing of $C_{18}$-$(PEP_{Au}^{M-ox})_2$ within the fibers. XRD patterns of aligned $C_{18}$-$(PEP_{Au}^{M-ox})_2$ fibers displayed the prototypical pattern observed for cross-β amyloidlike structure (FIGS. 5 and 21). An intense meridional reflection corresponding to a d-spacing of 4.6 angstroms was attributed to the H-bonding distances between peptide backbones. The off-meridian reflections corresponding to a d-spacing of 4.2 is attributed to the distance between diagonal planes (FIG. 21b). Equatorial peaks with d-spacings of ~6.5, ~9, and ~18 angstroms corresponded to repeat distances between β-sheets (FIGS. 5 and 21c).

Figures 6A, 6B, 6C, 6D, 6E:
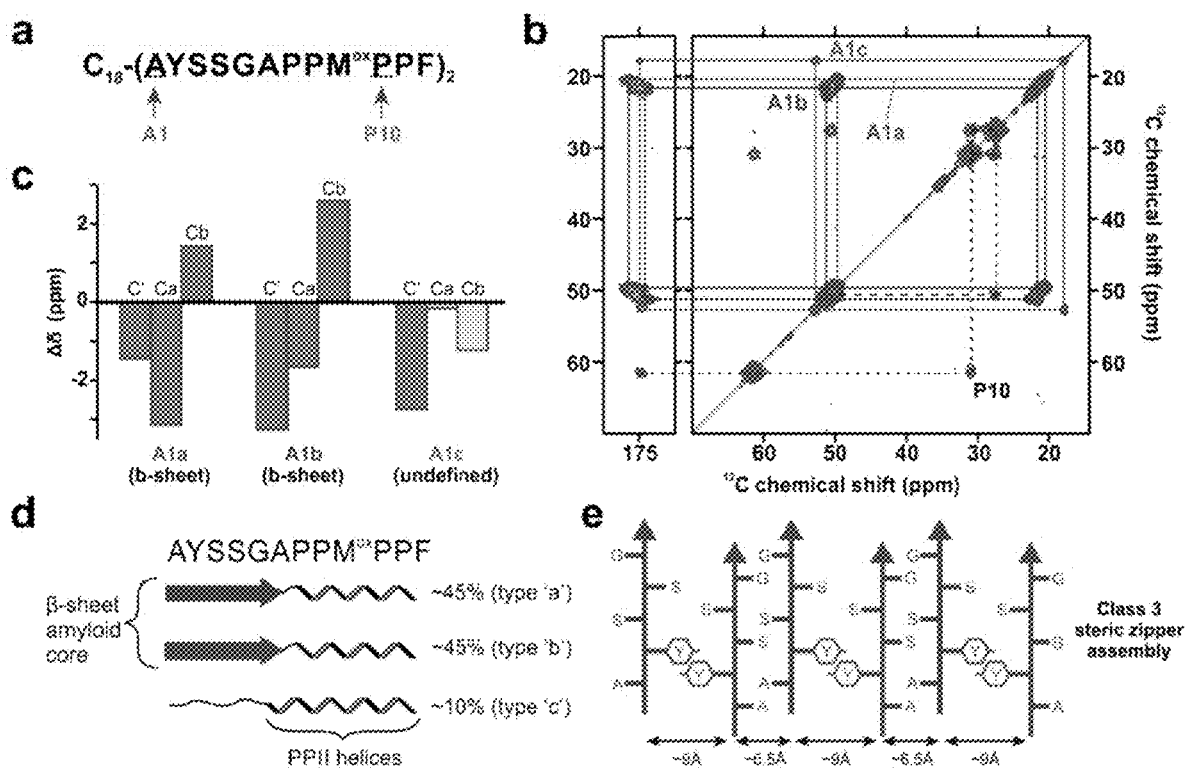
FIGS. 6A-6E: MAS ssNMR results.
Figures 22A, 22B, 22C, 22D, 22E:
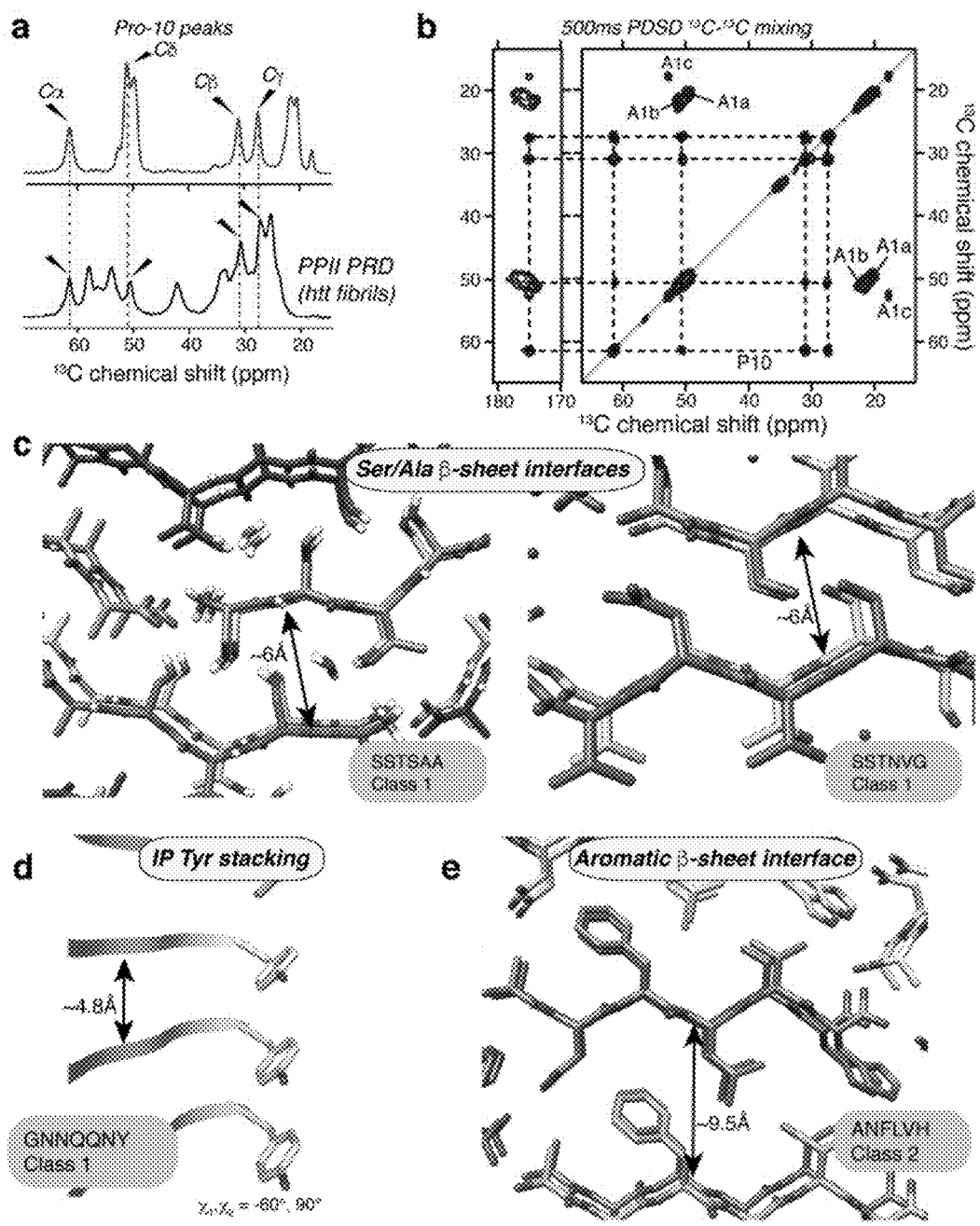
FIGS. 22A-22E: Additional ssNMR results and structural reference.

The CD, FTIR, and XRD data revealed that the peptide-based core of the assemblies was stabilized by substantial β-strand formation, but the location of the β-strand within the peptide was uncertain. To address this, ssNMR was applied to site-specifically labeled $C_{18}$-$(PEP_{Au}^{M-ox})_2$ assemblies. To probe the very N-terminal end of the peptide, $^{13}C$, $^{15}N$-labeling was applied to the A1 residue. To probe the Pro-rich C-terminal half of the peptide, a $^{13}C$, $^{15}N$-labeled P10 was also included in the same peptide (FIG. 6a). FIG. 6b shows a 2-D magic-angle spinning (MAS) ssNMR spectrum obtained for labeled $C_{18}$-$(PEP_{Au}^{M-ox})_2$ assemblies. The off-diagonal cross-peaks provide residue-specific assignments of each labeled residue. The P10 peaks (black dashed lines) have chemical shifts indicative of a PPII helix structure (FIG. 22a). The observation of a single set of peaks shows that P10 has the same PPII structure in all the $C_{18}$-$(PEP_{Au}^{M-ox})_2$ in the sample. In contrast, A1 features multiple sets of peaks, indicating the presence of multiple structures. The dominant A1 peaks (A1a and A1b), accounting for ~90% of the signal, have chemical shifts that indicate A1 to be part of the β-sheet structure (FIG. 6c). The A1c conformer was present at much lower intensity (~10% of the total signal), lacks β-sheet shifts, and presumably reflects peptide that failed to incorporate into the amyloid-like core (e.g. the pseudospherical aggregates observed in TEM images). In long-mixing ssNMR data these three conformers show no sign of dynamics- or proximity-enabled polarization exchange (FIG. 22b). Motion-sensitive ssNMR experiments (not shown) indicate that all sites are relatively rigid and immobilized in the peptide assemblies. Therefore, two structurally different peptide conformers, present at 1:1 ratio, make up ~90% of the sample (FIG. 6d). The ssNMR shows that the β-sheet structure extends to the very N-terminal residue A1. At the other end P10 is outside the β-sheet, forming instead part of a PPII helix that presumably involves much of the Pro-rich C-terminal peptide end.

How do two equally populated β-sheet/PPII peptide building blocks (FIG. 6d) co-assemble into the β-sheet-based core of the assemblies described herein? The X-ray cross-β pattern showed ~6.5 and ~9 Å intersheet distances between β-sheets. Sheet-to-sheet interfaces in amyloid structures have been characterized as 'steric-zippers' classified into distinct symmetry classes. The structural data, self-assembly behavior, and chemical nature of $C_{18}$-$(PEP_{Au}^{M-ox})_2$ point to a likely architecture of the assemblies. The $C_{18}$ acyl tails work to bring the peptide conjugates together to form micellar structures early in the assembly process. Clustering of the $C_{18}$ tails dictates a parallel alignment of the self-assembling peptides and thus facilitates the formation of β-sheets that are co-aligned and parallel in nature. This fits well with the FTIR data and ssNMR results described herein. Only a class 3 zipper explains the doubled β-sheet ssNMR peaks and their 1:1 intensity ratio as it predicts structural differences between two types of co-assembling β-sheets. In addition, class 3 zippers also predict the presence of two types of intersheet interfaces, which feature either the odd-numbered or the even-numbered residues (FIG. 6e). The odd-residue interface features only small side chains (Ala/Ser/Gly), which enable the formation of a tight inter-sheet interface that places the sheets ~6.5 Å apart (FIG. 22c). The even-numbered interface includes the large aromatic Tyr. In amyloid-like crystal structures with parallel β-sheets, such Tyr rings adopt a characteristic ring-stacked orientation, as shown in FIG. 22d. The bulkiness of the aromatic rings causes notably wide sheet-to-sheet interfaces that are ~9-10 Å apart (e.g. FIG. 22e), in line with the peptide assemblies X-ray pattern. Thus, this kind of assembly provides an elegant rationale for the ssNMR, FTIR, as well as X-ray results, and demonstrates a peptide core structure that combines packed PPII helical C-termini with a class 3 amyloid-like assembly.

Figures 7A, 7B, 7C, 7D:
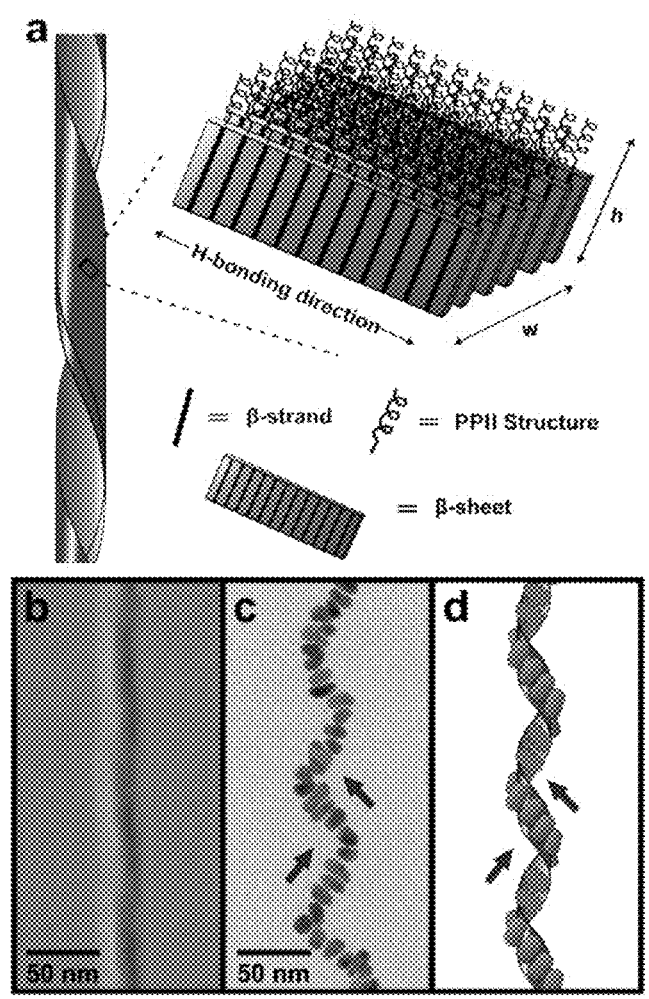
FIGS. 7A-7D: $C_{18}$-$(PEP_{Au}^{M-Ox})_2$ Assembly Model.
Figure 17:
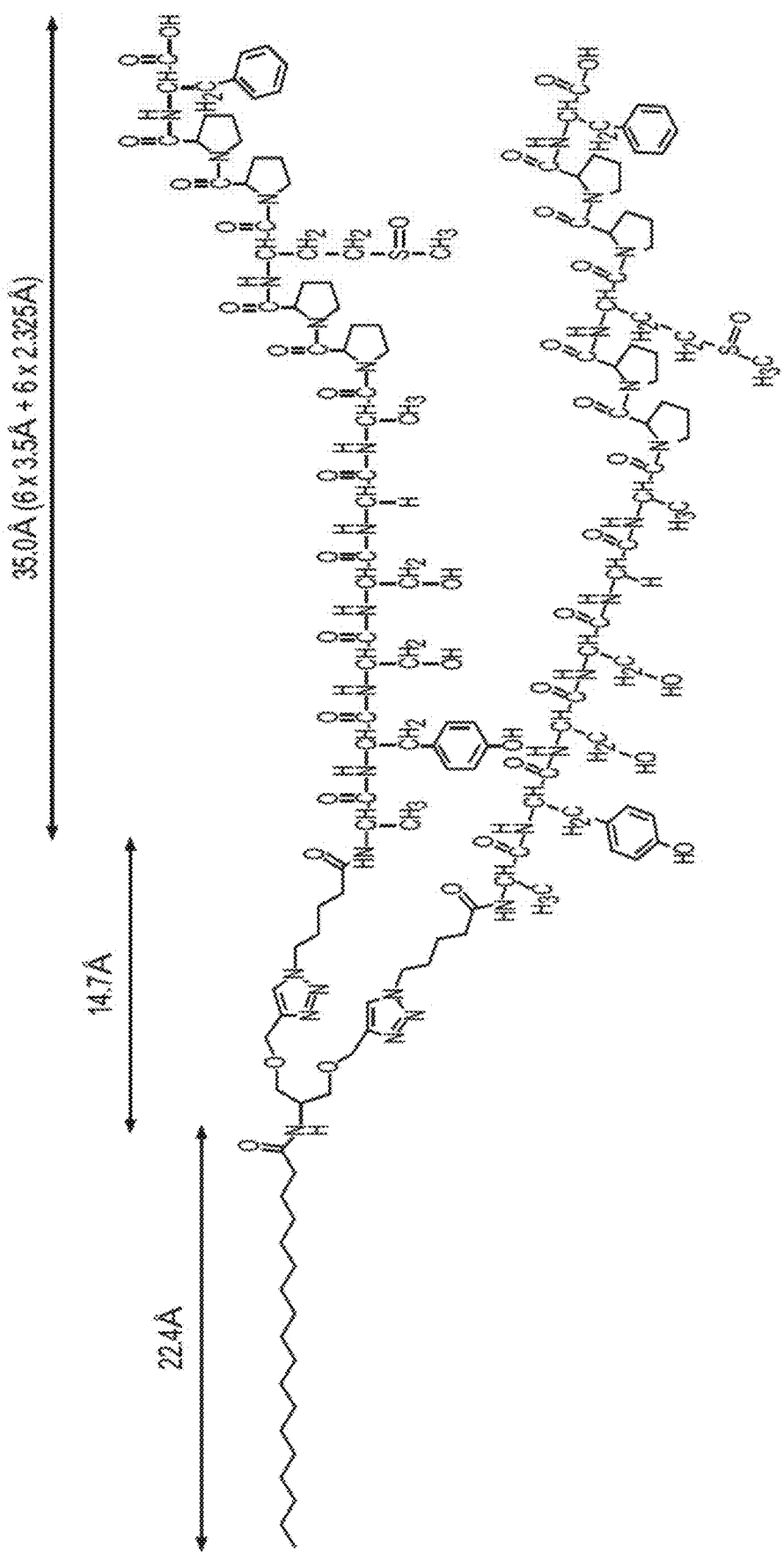
FIG. 17: Length of the different extended segments of $C_{18}$-$(PEP_{Au}^{M-Ox})_2$. The total length of the extended molecule is ~7 nm.
Figure 18:
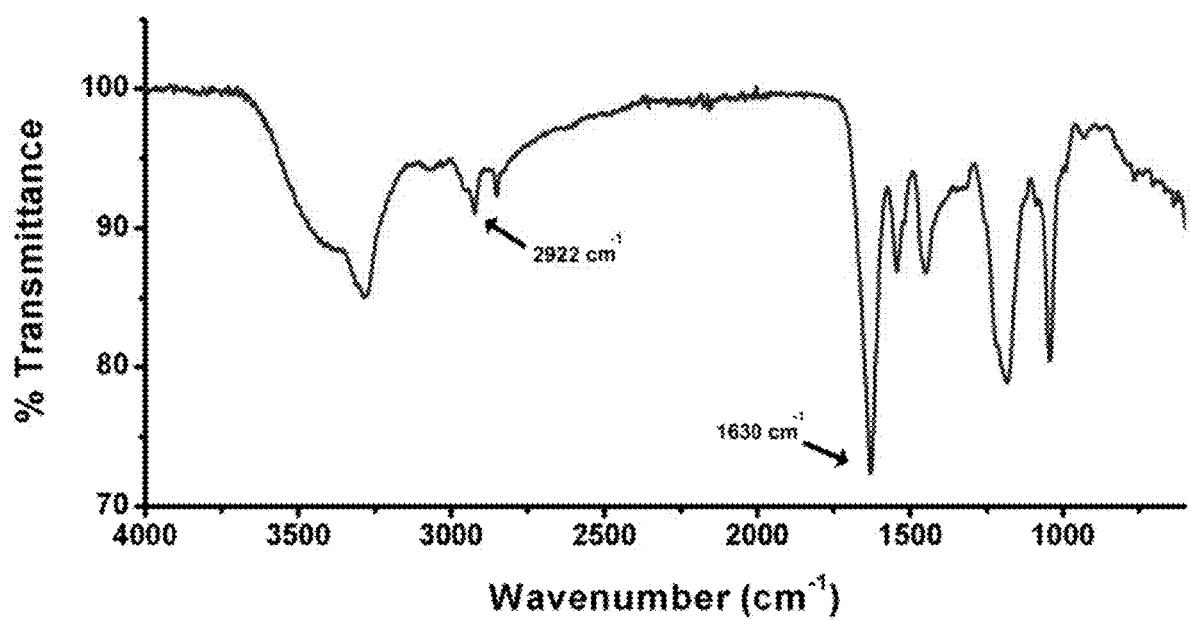
FIG. 18: IR spectrum of $C_{18}$-$(PEP_{Au}^{M-Ox})_2$ fibers. Peaks at 1630 cm−1 and 2922 $cm^{-1}$ correspond to the amide I band and C—H stretch, respectively.
Figure 19A:
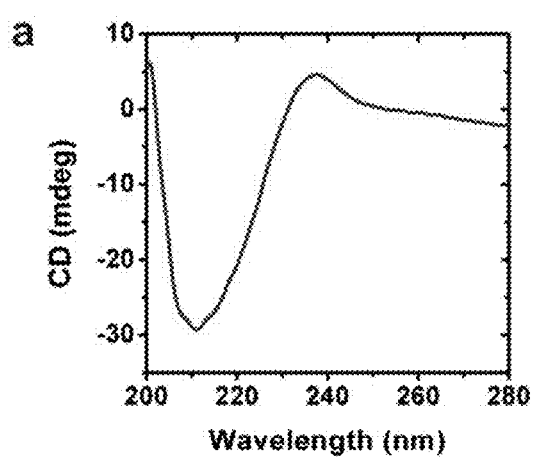
FIGS. 19A-19B.
Figure 19B:
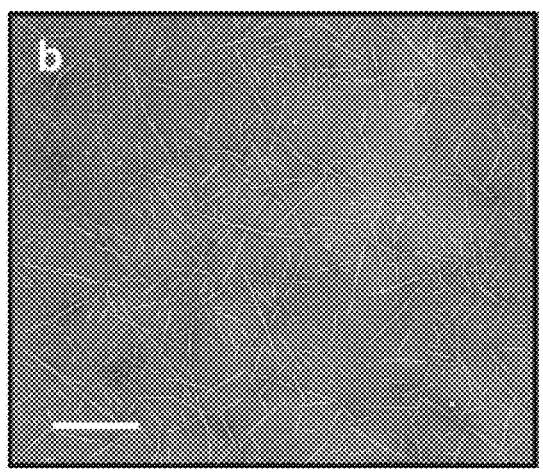

Single Helix Assembly Model. Taking into account the accumulated data on the $C_{18}$-$(PEP_{Au}^{M-ox})_2$ assemblies, a molecular packing model is proposed for the helical ribbon (FIG. 7a). The ribbon consists of a monolayer of $C_{18}$-$(PEP_{Au}^{M-ox})_2$ arranged perpendicular to the faces in a cross-β architecture. This allows the PPII helix and negatively charged carboxylates (at pH ~7) to be exposed on the outer surface of the helical ribbon. The model adheres to the ribbon vertical thickness constraint of ~4 nm, as measured by AFM. Since the extended length of $C_{18}$-$(PEP_{Au}^{M-ox})_2$ is estimated to be ~7 nm (FIG. 17), a bilayer structure where the alkyl chains are interdigitated in the core of the ribbon would not be possible. It is proposed that the aliphatic chains, which are relatively ordered, aggregate with one another at the inner surface of the helical ribbon or possibly fold inward with one another in-between β-sheets. In either case, the helical ribbon architecture segregates the relatively hydrophobic N-terminus from the aqueous buffer while exposing the hydrophilic C-terminus. This is in contrast to a twisted ribbon structure where both sides of the tape would be equally exposed. The ribbon width, w, is determined by the number of β-sheets stacked side-by-side with regular ~6.5 and ~9 Å distances. Previous reports have shown that helical ribbon structures typically precede the formation of nanotubes through ribbon width growth, but in this case the helical ribbon likely represents a kinetic product as no further 'closing' of the helices was observed.

Based on this assembly model and the structural parameters of both the single helices and $C_{18}$-$(PEP_{Au}^{M-ox})_2$ fibers, it was concluded that the metal (i.e., gold) nanoparticles decorate the outer face of the helical ribbon (FIGS. 7b-d). Careful inspection of the nanoparticle orientation within the superstructures (FIG. 7c) indicates that the rod-like particles align in parallel along the width of the ribbons, which supports a model where particle growth proceeds in one-direction (FIG. 7d) and could be limited by the width of the helical ribbon. The regular distances between the particles could be due to electrostatic repulsion between particles.

Since it is proposed that the C-termini of $C_{18}$-$(PEP_{Au}^{M-ox})_2$ are exposed at the outer face of the helical ribbon, it is reasoned then that the particles must be bound to the residues that make up the PPII helix. Previous reports on $PEP_{AU}$ binding onto gold surfaces conclude that Tyr-2 and Phe-12 bind most strongly to the 111 facets of gold nanoparticles due to their aromatic side chains. Since the Tyr-2 molecules are integral to the parallel β-sheet structure within the core of the peptide ribbon, the exposed phenylalanine at the C-terminus must account for much of the binding between the gold particles and the peptide assembly. In addition, methionine residues, which also bind strongly, could contribute to the overall binding interaction. The inner surface of the helical ribbon is sterically hindered, which prevents particle binding.

Various embodiments are described herein. The specific embodiments are not intended as an exhaustive description or as a limitation to the broader aspects discussed herein. One aspect described in conjunction with a particular embodiment is not necessarily limited to that embodiment and can be practiced with any other embodiment(s).

Definitions

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, the term "aliphatic" or "alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In certain embodiments, an alkyl comprises one to six carbon atoms (e.g., $C_1$-$C_6$ alkyl). In certain embodiments, an alkyl comprises two to eight carbon atoms (e.g., $C_2$-$C_8$ alkyl). In certain embodiments, an alkyl comprises two to six carbon atoms (e.g., $C_2$-$C_6$ alkyl). In certain embodiments, an alkyl comprises one to three carbon atoms (e.g., $C_1$-$C_3$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like.

The term "aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. In some embodiments, aryl group has 6- to 10-carbon atoms. Aryl groups include, but are not limited to, groups such as phenyl, fluorenyl, and naphthyl.

The term "heteroaryl" refers to a radical derived from a 5- to 18-membered aromatic ring radical that comprises one to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. In some embodiments, the heteroatom(s) in the heteroaryl radical is optionally oxidized. In some embodiments, one or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno [2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). In some embodiments, the term "substituted heteroaryl" is meant to include heteroaryl radicals as defined above which are substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $-R^c-OR^a$, $-R^c-SR^a$, $-R^c-OC(O)-R^b$, $-R^c-N(R^a)_2$, $-R^c-C(O)R^a$, $-R^c-C(O)OR^a$, $-R^c-C(O)N(R^a)_2$, $-R^c-O-R^d-C(O)N(R^a)_2$, $-R^c-N(R^a)C(O)OR^a$, $-R^c-N(R^a)C(O)R^a$, $-R^c-N(R^a)S(O)_2R^b$, $-R^c-S(O)_2OR^a$ and $-R^c-S(O)_2N(R^a)_2$, where each $R^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each $R^b$ is independently alkyl, fluoroalkyl, carbocyclyl, carbocyclylalkyl, aryl, aralkyl, heterocyclyl, heterocyclylalkyl, heteroaryl or heteroarylalkyl, and each $R^c$ is independently a direct bond or a straight or branched alkylene, alkenylene, or alkynylene chain.

The terms "optional" or "optionally" mean that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

The following examples are given to illustrate the present invention. It should be understood, however, that the invention is not to be limited to the specific conditions or details described in these examples.

EXAMPLES

Materials and Methods. All chemicals were purchased from a commercial source, such as Aldrich or Fisher, and used without further purification. $N_3$—$C_4H_8CO$-AY-SSGAPPMPPF ($N_3$-$PEP_{Au}$) was synthesized by Pierce Biotechnology, Inc. Triethylammonium acetate buffer (TEAA) was purchased from a commercial source, such as Aldrich (catalog number: 90358) and 4-(2-hydroxyethyl)-1-piperazineethanesulfonic acid (pH=7.3) (HEPES) buffer was purchased from a commercial source, such as Fisher Scientific (catalog number: BP 299-100). Chloroauric acid ($HAuCl_4$) was purchased from a commercial source, such as Sigma-Aldrich (catalog number: 520918).

Peptide conjugates were purified using an Agilent 1200 Series reverse-phase high-pressure liquid chromatography (HPLC) instrument equipped with an Agilent Zorbax 300SB-C18 column. Peptide conjugates were quantified based on their absorbance at 280 nm and using the extinction coefficient for tyrosine (1280 $M^{-1}cm^{-1}$). UV-Vis spectra were collected using an Agilent 8453 UV-Vis spectrometer equipped with deuterium and tungsten lamps. Matrix assisted laser desorption ionization time-of-flight mass spectrometry (MALDI-TOF MS) data were collected using an Applied Biosystem Voyager System 6174 MALDI-TOF mass spectrometer (positive reflector mode; accelerating voltage: 20 kV) and using α-cyano-4-hydroxycinnamic acid (CHCA) as the ionization matrix. Nanopure water (NP $H_2O$, 18.1 MS2) was obtained from a Barnstead Diamond™ water purification system.

Example 1

Preparation of $N_3$-$PEP_{Au}^{M-Ox}$ $N_3$-$PEP_{Au}$ (3 mg, 2.23 μmol) was dissolved in a 1:1 mixture of $CH_3CN$:NP $H_2O$. To this solution concentrated $H_2O_2$ was added to bring the final $H_2O_2$ concentration to 100 mM. The solution was vortexed and left undisturbed for 8-15 hours. This final solution was purified using reverse-phase HPLC eluting with a linear gradient of 0.05% formic acid in $CH_3CN$ and 0.1% formic acid in NP $H_2O$ (5/95 to 95/5 over 30 min.), to produce $N_3$-$PEP_{Au}^{M-Ox}$.

Example 2

Synthetic Protocol of Single Helices

In a plastic vial, $C_{18}$-$(PEP_{Au}^{M-Ox})_2$ (~18.7 nmol) was dissolved in 250 μL of 0.1 M HEPES buffer and sonicated for 5 min. After sonication, the solution was allowed to sit at room temperature for 25 min. A fresh stock solution of $HAuCl_4$ in TEAA buffer was prepared by mixing 100 μL of 0.1 M $HAuCl_4$ in NP $H_2O$ with 100 μL of 1M TEAA buffer. The resulting mixture was vortexed for 1 min. To the $C_{18}$-$(PEP_{Au}^{M-Ox})_2$ solution, 2 μL of the freshly prepared $HAuCl_4$/TEAA solution was added. A dark cloud appeared 2-4 secs after the addition of the $HAuCl_4$/TEAA solution; at this point the vial was briefly vortexed and then left undisturbed at room temperature.

TEM images of silver nanoparticle single-helical superstructures are shown in FIG. 1. The arrows reveal clearly the helicity of the nanoparticle superstructures.

Example 3

Synthetic Protocol of Palladium Nanoparticle Superstructures

In a plastic vial, $C_{18}$-$(PEP_{Au}^{M-Ox})_2$ (~18.7 nmol) was dissolved in 250 μL of 0.1 M HEPES buffer and sonicated for 5 min. After sonication, the solution was allowed to sit at room temperature for 25 min. A fresh 0.1 M $NaBH_4$ solution was prepared. To the $C_{18}$-$(PEP_{Au}^{M-Ox})_2$ solution, 2.5 μL of the $NaBH_4$ solution was added followed by 1 μL of 0.1 M $Pd(NO_3)_2$ (aq.) solution. Upon addition of the $Pd(NO_3)_2$ solution, a 'dark cloud' was observed, and the solution was briefly vortexed immediately and then left undisturbed at room temperature.

Figures 2A, 2B:
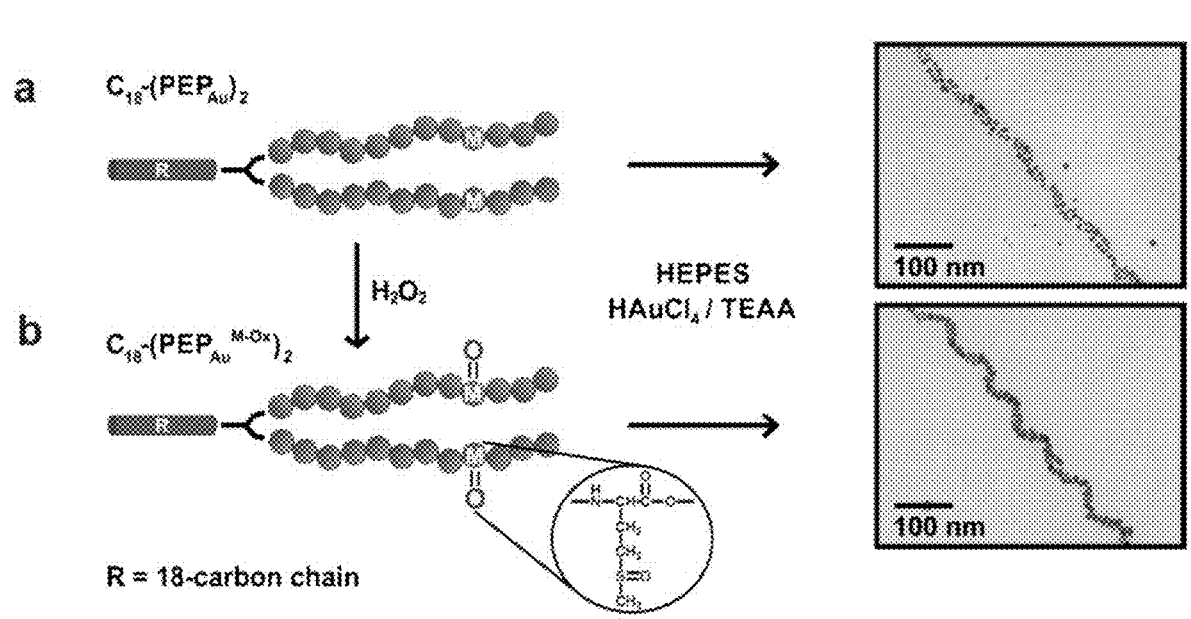
FIGS. 2A-2B shows a reparation of nanoparticle superstructures.

TEM images of palladium nanoparticle superstructures are shown in FIG. 2.

Example 4

Preparation of $C_{18}$-$(PEP_{Au}^{M-Ox})_2$ Fibers

75 μM solutions of $C_{18}$-$(PEP_{Au}^{M-Ox})_2$ fibers were prepared in 0.1 M HEPES buffer. For CD spectroscopy studies, 10 mM HEPES buffer was used. After one day of sitting at room temperature, the solutions were analyzed. For some CD and TEM experiments, $CaCl_2$ was added (1 mM final concentration) to accelerate fiber formation.

Transmission Electron Microscopy. TEM images were collected with a FEI Morgagni 268 (80 kV) with an AMT side mount CCD camera system. Phosphotungstic acid (pH 7.4) was used to stain TEM sample grids for the peptide assembly studies. TEM samples were prepared by dropcasting 6 μL of solution onto a 3-mm-diameter copper grid coated with formvar. After 5 min., the excess solution was wicked away. The grid was washed with NP $H_2O$ (6 μL) and wicked away after 1 min.

Cryo-Electron Tomography and 3-D Reconstruction. For the single-helical gold nanoparticle superstructures, 4 μL solution was applied to the carbon side of glow discharged perforated R2/2 Quantifoil grids (Quantifoil Micro Tools, Jena, Germany) before plunge-freezing using a manual gravity plunger. A series of images were recorded by tilting the specimen from −60° to 70° in increments of 3° (<45°) and 2° (>45°). Images were recorded on a FEI Falcon II direct electron detector camera at a nominal magnification of 39,000×. Altogether, 51 images were collected in one tilt series with a total dose of ~50 e−/Å². Images were recorded at a defocus value of ~0.5 μm using FEI batch tomography software. The IMOD package72 was used to align tilted projection images and reconstruct the final 3D density map from the aligned image stack. For surface rendering, the tomogram was filtered to 20 Å resolution and displayed using the program UCSF CHIMERA.

Atomic Force Microscopy. AFM images were collected with an Asylum MFP-3D atomic force microscope using tapping-mode. Images were obtained using ultrasharp AFM tips (Nano-and More, SHR-150), with 1 Hz scanning rate. The APTESmica was prepared by drop-casting 0.1% APTES solution in NP $H_2O$ onto freshly cleaved mica and after 10 min., the mica was rinsed with NP $H_2O$. $C_{18}$-$(PEP_{Au}^{M-Ox})_2$ was dissolved in 0.1 M HEPES (75 μM) and allowed to sit at room temperature overnight. After 1 day of incubation, 20 μL of the solution was drop-cast onto the APTES-functionalized mica. After 1 min., the sample was rinsed with NP $H_2O$ and allowed to air dry overnight.

Attenuated Total Reflectance Fourier Transform Infrared Spectroscopy. ATRFTIR spectra were collected on a PerkinElmer Spectrum 100 FTIR instrument with a universal attenuated total reflectance-sampling accessory coupled to a computer using PerkinElmer Spectrum Express software. The sample was background corrected in air. $C_{18}$-$(PEP_{Au}^{M-Ox})_2$ was dissolved and sonicated in 0.1 M HEPES (75 μM). After 1 day, the assembled fibers were dialyzed three times in NP $H_2O$ using d-tube dialyzers (Millipore, catalog number: 71505-3) to remove the buffer, and the fibers were concentrated. The concentrated solution containing the fibers was then drop-cast onto the ATR-FTIR substrate and al-lowed to air dry.

Circular Dichroism Spectroscopy. CD measurements were conducted on an Olis DSM 17 CD spectrometer. The scan rate was 8 nm/min. and the bandwidth was 2 nm. All CD experiments were carried out in 10 mM HEPES (peptide assembly; 200-280 nm) or 0.1 M HEPES (nanoparticle assembly; 450-800 nm) with a 1 mm path length quartz cuvette at 25° C.

Powder X-ray Diffraction. Powder X-ray diffraction was performed on a Bruker X8 Prospector Ultra diffractometer equipped with APEX II CCD detector and an 1 μS microfocus CuKα source (λ=1.54178 Å). The diffractograms were recorded at a distance of 15 cm at room temperature. Raw data were retrieved using PILOT plug-in in Bruker APEX II software package and further processed in Match! Software to obtain d and intensity values. The sample was prepared by dissolving ~1.5 mg of $C_{18}$-$(PEP_{Au}^{M-Ox})_2$ in 1 mL 0.1 M HEPES and sonicating for 5 min. The samples were left to sit overnight. After 24 hrs., the solution was ultracentrifuged (rmax=213,000×g) for 1 hr. The supernatant was removed and NP $H_2O$ (1 mL) was added and the samples were ultra-centrifuged again at the same speeds. After centrifugation, the supernatant was removed leaving behind a clear gel. The peptide gel was loaded into a glass capillary (φ=0.7 mm) and air-dried.

MAS Solid-State NMR Spectroscopy. Labeled $N_3$-PEPAu was purchased from Pierce Custom Peptides and labeled $C_{18}$-$(PEP_{Au}^{M-Ox})_2$ was synthesized according to the protocols detailed above. Labeled $C_{18}$-$(PEP_{Au}^{M-Ox})_2$ fibers (2 mg) were packed into thin wall 3.2 mm zirconia MAS rotors (Bruker Biospin, Billerica, Mass.) by ultracentrifugation at ~130,000 g in a home-built sample packing tool spun in a Beckman Coulter Optima L-100 XP ultra-centrifuge equipped with a SW-32 Ti rotor. MAS ssNMR spectra were obtained with a widebore Bruker Avance I NMR spectrometer operating at a 1H Larmor frequency of 600 MHz (14.1 T) using a 3.2 mm HCN MAS ssNMR probe equipped with a "EFree" reduced electric field coil (Bruker Biospin). Sample temperature was maintained at 277K using a constant flow (800 L/h) of cooled gas. Bruker Topspin software was used to acquire the spectra. Spectra were processed using NMRPipe software and analyzed with CCPNMR/Analysis. The $^{13}C$ signals of adamantine were used to externally reference samples to 4,4-dimethyl-4-silapentane-1-1 sulfonic acid (DSS). 1-D and 2-D ssNMR spectra were acquired at 10 kHz MAS, using ramped $^1H$—$^{13}C$ cross-polarization (CP) with a 2.0 ms CP contact time, a 3 s recycle delay, and 83 kHz two-pulse phase-modulated (TPPM) decoupling. A total of 1024 scans were obtained for the 1-D CP experiment. The short-mixing $^{13}C$—$^{13}C$ 2-D spectrum was obtained with 20 ms of dipolar assisted rotational resonance (DARR) $^{13}C$—$^{13}C$ mixing. The 2-D spectrum in the SI featured 500 ms of $^{13}C$—$^{13}C$ proton-driven spin diffusion (PDSD), which is expected to allow longer-range signal transfer over up to 6-7 Å. Additional experimental details are summarized in Table 1, below (details experimental conditions of the MAS ssNMR experiments. Abbreviations: NS, number of scans; Set Temp, set temperature of cooling gas; MAS, magic angle spinning rate; RD, recycle delay; TPPM, two-pulse phase-modulated 1H decoupling power during evolution and acquisition).

TABLE 1

| FIG. | Expt. | NS | Set Temp (K) | MAS (kHz) | RD (s) | TPPM (kHz) | $t_1$ evol. (μs) | DARR mixing time (ms) | $^1H$-$^{13}C$ Contact time (ms) |
|---|---|---|---|---|---|---|---|---|---|
| 6b | 2D $^{13}C$-$^{13}C$ CP-DARR | 64 | 277 | 10 | 3 | 83 | 562*35.6 | 20 | 2 |
| 22a | $^1H$-$^{13}C$ CP | 1024 | 277 | 10 | 3 | 83 | NA | NA | 2 |
| 22b | 2D $^{13}C$-$^{13}C$ PDSD | 64 | 277 | 10 | 3 | 83 | 562*33.11 | 500 | 2 |

Example 5

Additional Conjugate Synthesis $C_{14-22}$-$(PEP_{Au}^{M-Ox})_2$, $N_3$-$(PEP_{Au}^{M-Ox})$, and all organic intermediates were synthesized and purified by employing previously reported protocols from Merg et al., Langmuir, 31:9492-9501 (2015) and Merg et al., J. Am. Chem. Soc., 138:13655-13663 (2016). Briefly, fatty acids were activated by employing standard NHS activation strategy. The corresponding functionalized NHS esters were treated with 2-amino-1,3-propanediol. The resultant diols were reacted with propargyl bromide to obtain the dialkyne organic substrate. All final dialkyne organic intermediates were characterized via LC-MS (Table S1). Commercially obtained $N_3$-$(PEP_{Au})$ was dissolved in 1:1 Nanopure water and acetonitrile. Concentrated $H_2O_2$ was added to this solution to bring the final concentration of $H_2O_2$ equal to 100 mM. The resultant oxidized product was purified via HPLC. Purified $N_3$-$(PEP_{Au}^{M-ox})$ was ultimately coupled with each dialkyne organic substrate using standard Cu-catalyzed click chemistry and purified via HPLC. Each purified peptide conjugate was characterized via LC-MS spectrometry.

Peptide Conjugate Assembly

Purified peptide conjugates were lyophilized (18.7 nmol) and dissolved in 250 μL of 0.1 M HEPES buffer. The solution was sonicated for 5 minutes. Thereafter, an aliquot of 0.1 M $CaCl_2$ solution was added to bring the final concentration of $CaCl_2$ to 1 mM. TEM samples were prepared after ~16 hours.

Figures 23A, 23B, 23C:
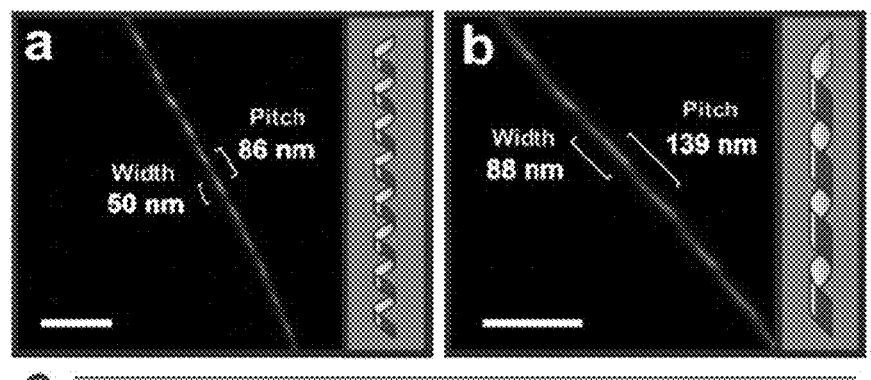
FIGS. 23A-23C: Effect of aliphatic tail length on helical ribbon morphology. AFM images of FIG. 23(a) $C_{16}$ and FIG. 23(b) $C_{22}$ helical ribbons, showing differences in ribbon width and pitch length (scale bar=200 nm). (c) Average ribbon width and pitch lengths of $C_{16-22}$ helical ribbons.

Atomic force microscopy (AFM) was employed to discern the morphology of the peptide conjugate fibers. AFM images of $C_{16-22}$ revealed left-handed helical ribbons. The measured average ribbon width and pitch increases with aliphatic tail length, as shown in FIGS. 23(a)-23(c). The ribbon thickness of $C_{16-22}$ fiber assemblies is between ~3-4 nm, which is roughly equal to the length of the peptide head group after considering its secondary structure. Fiber width data obtained from TEM analysis and ribbon height data exclude the possibility of $C_{16-22}$ packing into a bilayer configuration. The microscopic evidence suggests that all observed fibers are helical ribbons where the ribbon consists of a monolayer of assembled peptide conjugate molecules.

Nanoparticle Superstructure Preparation

Lyophilized conjugates, $C_x$-$(PEP_{Au}^{M-ox})_2$, (18.7 nmol for x=14-20, and 9.4 nmol for x=22) were dissolved in 250 µL of 0.1 M HEPES buffer. The solution was sonicated for 5 minutes. After 25 minutes, 2 µL of vortexed solution of 1:1 mixture of aqueous 0.1 M $HAuCl_4$ in 1 M TEAA buffer was added to the peptide conjugate solution. A black cloud was observed after 2-3 seconds and the vial was then immediately vortexed. For helices derived from $C_{16}$-$(PEP_{Au}^{M-ox})_2$, 2.5 µL of 0.1 M $CaCl_2$ was added to the peptide conjugate solution after sonication to yield a 1 mM $CaCl_2$ solution. TEM samples were prepared after ~16 hours.

Figures 24A, 24Q:
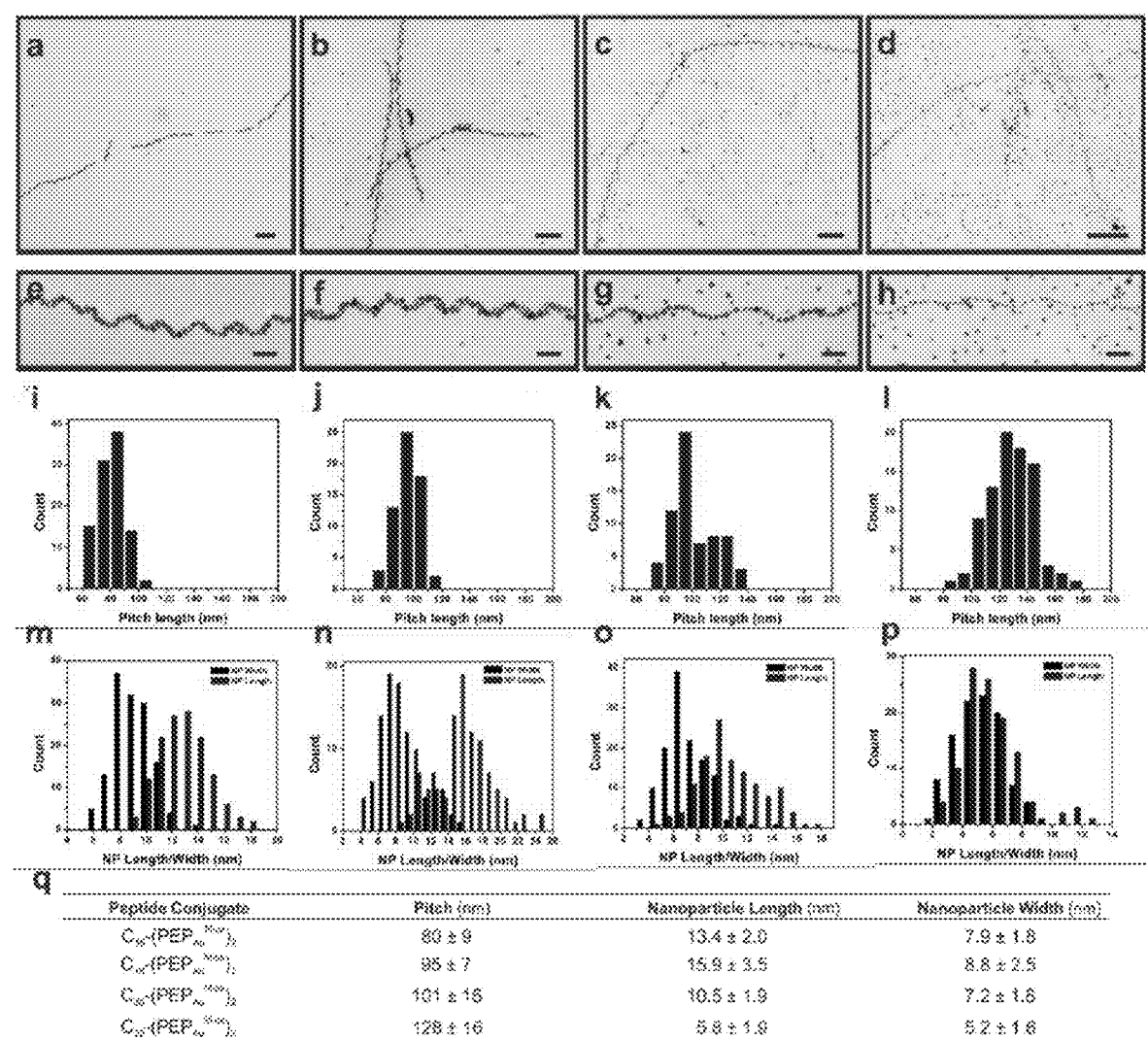
FIGS. 24A-24Q: Effect of aliphatic tail length on helical pitch and nanoparticle size and shape in a family of single-helical superstructures. Low magnification TEM images of single helices derived from FIG. 24(a) $C_{16}$, FIG. 24(b) $C_{18}$, FIG. 24(c) $C_{20}$, and FIG. 24(d) $C_{22}$ (scale bar: 200 nm). High magnification TEM images of single helices derived from FIG. 24(e) $C_{16}$, FIG. 24(f) $C_{18}$, FIG. 24(g) $C_{20}$, and FIG. 24(h) $C_{22}$ reveal an increase in helical pitch and decrease in nanoparticle size with increase in aliphatic tail length (scale bar: 50 nm). Helical pitch distributions of FIG. 24(i) $C_{16}$, FIG. 24(j) $C_{18}$, FIG. 24(k) $C_{20}$, and FIG. 24(l) $C_{22}$-based single helices. Nanoparticle length and width distributions of FIG. 24(m) $C_{16}$, FIG. 24(n) $C_{18}$, FIG. 24(o) $C_{20}$, and FIG. 24(p) $C_{22}$-based single helices.

As shown in FIG. 24, for $C_{16}$, gold nanoparticle single helices with an average pitch length of 80±9 nm resulted. $C_{18-20, 22}$ yielded single helices with average pitch values of 95±7, 101±15 and 128±16 nm, respectively.

G-factors corresponding to $C_{16-20}$ directed single-helical superstructures indicate a decrease in chiroptical activity with increase in aliphatic tail length, as shown in Table 2.

TABLE 2

| Peptide conjugate | g-factor |
|---|---|
| $C_{16}$-$(PEP_{Au}^{M-ox})_2$ | 0.0178 |
| $C_{18}$-$(PEP_{Au}^{M-ox})_2$ | 0.0177 |
| $C_{20}$-$(PEP_{Au}^{M-ox})_2$ | 0.0002 |

Example 6

$C_{14}$-Helices

Figure 25:
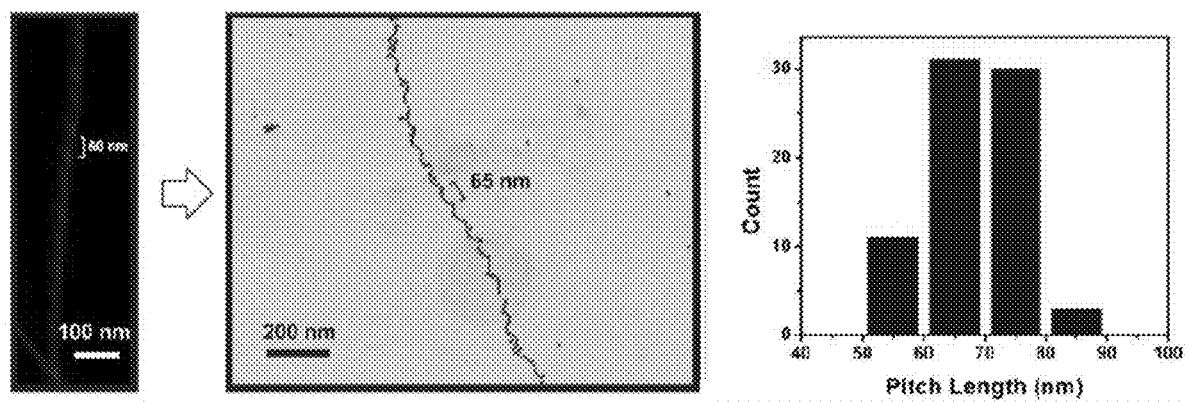
FIG. 25: introducing more hydrophobic amino acid residues is shown, as explained in Example 6.

A modified sequence of $PEP_{Au}^{M-ox}$ was made by introducing more hydrophobic amino acid residues into the N-terminal region. In one specific example, we modified the 'wild-type' $PEP_{Au}^{M-ox}$ (AYSSGAPPM$^{ox}$PPF) to AYSFGAPPM$^{ox}$PPF, where one serine residue has been replaced with a phenylalanine. Using this peptide, $C_{14}$-(AYSFGAPPM$^{ox}$PPF)$_2$ was prepared. This conjugate assembles into fibers, as evidenced by AFM and TEM studies, and the average pitch of the fibers is ~63-64 nm, indicating that the $C_{14}$ tail did indeed lead to a smaller pitch value. These conjugates can direct the assembly of gold nanoparticles into single-helical gold nanoparticle assemblies with a pitch of 67±6 nm. FIG. 25 shows this advance.

Example 7

Modified Oxidized Methionine Residue

Figure 26:
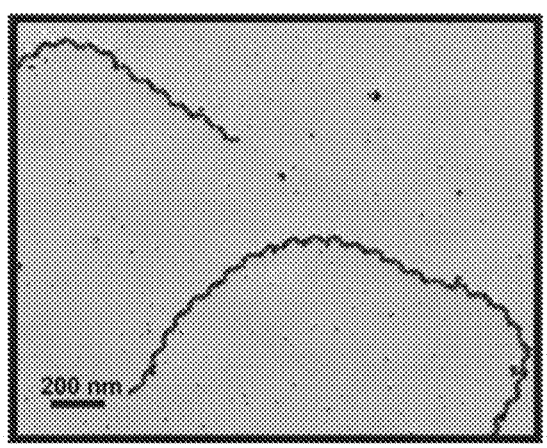
FIG. 26: modification of the position of the oxidized methionine residue is shown, as explained in Example 7.
Figure 26:
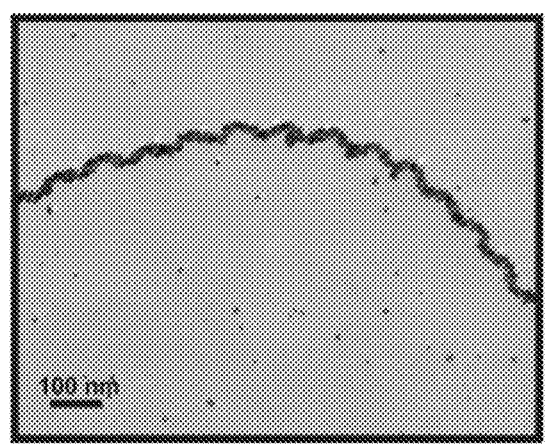
Figure 26:
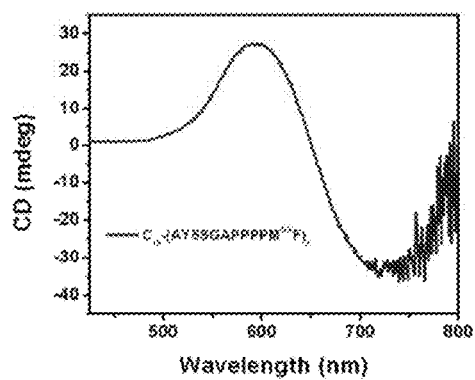

A residue with a modified position of the oxidized methionine residue was synthesized, which increased the density of nanoparticles within the helices. In one example, AYSSGAPPPPM$^{ox}$F, where the oxidized methionine was placed at the 11 position instead of the 9 position was prepared. The resulting conjugate, $C_{18}$-(AYSFGAPPPPM$^{ox}$F)$_2$, directs the formation of gold nanoparticle single helices with a high density of gold nanoparticles. These helices show very strong chiroptical activity. TEM images of the helices and their CD spectrum are shown in FIG. 26

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A metal nanoparticle superstructure, wherein:
   the superstructure comprises a plurality of metal nanoparticles, and
   the plurality of metal nanoparticles are positioned in an essentially single helical assembly.

2. The metal nanoparticle superstructure of claim 1, wherein the single helical assembly comprises a helical pitch of about 75 to about 115 nm.

3. The metal nanoparticle superstructure of claim 1, wherein an interparticle distance between metal nanoparticles in the metal nanoparticle superstructure is less than about 4 nm.

4. The metal nanoparticle superstructure of claim 1, wherein the metal nanoparticles have a length to width ratio of greater than about 1.

5. The metal nanoparticle superstructure of claim 1, wherein the metal nanoparticles have a width of about 2 to about 16 nm and a length of about 8 to about 30 nm.

6. The metal nanoparticle superstructure of claim 1, wherein the plurality of metal nanoparticles comprises gold.

7. The metal nanoparticle superstructure of claim 1, wherein the plurality of metal nanoparticles comprises palladium or silver.

8. The metal nanoparticle superstructure of claim 1, wherein the metal nanoparticle superstructure is produced by contacting a metal or metal salt with a compound of the following formula I:

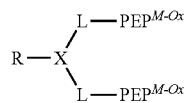

wherein:
R is a $C_6$-$C_{24}$ aliphatic or aromatic moiety;
X is an optional N-($C_1$-$C_5$) amide;
L is a linking moiety; and
$PEP^{M-Ox}$ is a peptide having an affinity to the metal or metal salt, where at least one methionine residue is oxidized.

9. The metal nanoparticle superstructure of claim 8, wherein $PEP^{M-ox}$ is AYSSGAPPM$^{ox}$PPF.

10. The metal nanoparticle superstructure of claim 8, wherein R is an $C^{14}$-$C^{20}$ aliphatic moiety.

11. A method for producing a metal nanoparticle superstructure comprising combining a metal or metal salt with a compound of the following formula I:

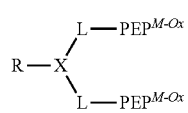

wherein:
R is a $C_6$-$C_{24}$ aliphatic or aromatic moiety;
X is an optional N-($C_1$-$C_5$) amide;
L is a linking moiety; and
$PEP^{M-ox}$ is a peptide having an affinity to the metal or metal salt, where at least one methionine residue in the peptide is oxidized.

12. The method of claim 11, wherein the metal salt is used, and is a salt comprising gold, a salt comprising silver or a salt comprising palladium.

13. The method of claim 11, wherein the metal or metal salt is combined with the compound of formula I in the presence of a buffering agent.

14. The method of claim 11, wherein $PEP^{M-ox}$ is AYSSGAPPM$^{ox}$PPF.

15. The method of claim 11, wherein R is an $C_{14}$-$C_{20}$ aliphatic moiety.

16. The method of claim 11, wherein the metal nanoparticle superstructure has a single helical assembly.

17. The method of claim 11, wherein the compound of formula (I) has the structure:

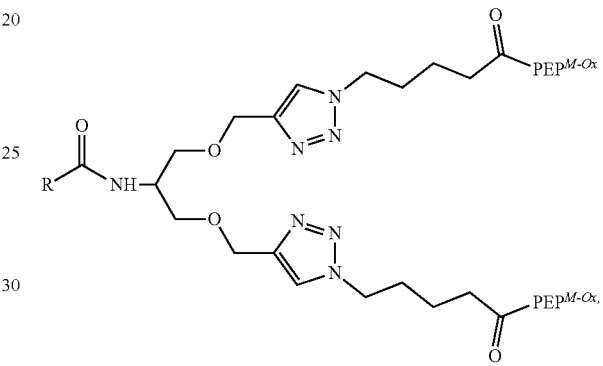

wherein R and $PEP^{M-ox}$ are as previously defined.

18. The method of claim 16, wherein the single helical assembly comprises a helical pitch of about 75 to about 115 nm.

19. The method of claim 11, wherein an interparticle distance between metal nanoparticles in the metal nanoparticle superstructure are less than about 4 nm.

20. The method of claim 11, wherein metal nanoparticles of the metal nanoparticle superstructure have a length to width ratio of greater than about 1.

21. A compound of the following formula:

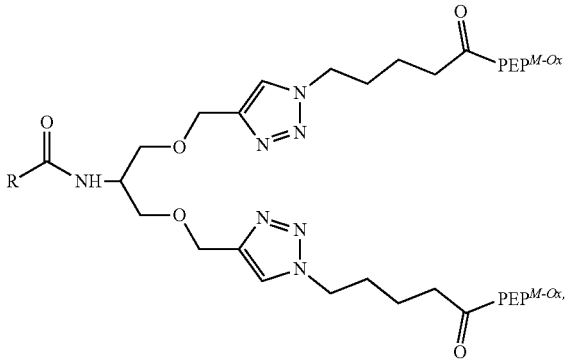

wherein:
R is a $C_6$-$C_{24}$ aliphatic or aromatic moiety; and
$PEP^{M-ox}$ is a peptide having an affinity to a metal or metal salt, where at least one methionine residue in the peptide is oxidized.

22. The compound of claim 21, wherein PEP$^{M\text{-}ox}$ is AYSSGAPPM$^{ox}$PPF.

23. The compound of claim 21, wherein the metal or metal salt comprises gold, silver, or palladium.

24. The compound of claim 21, wherein R is a $C_{16}$-$C_{24}$ aliphatic moiety.

\* \* \* \* \*